(12) United States Patent
Gray et al.

(10) Patent No.: US 12,270,057 B2
(45) Date of Patent: Apr. 8, 2025

(54) OPTIMIZED FIG4 GENES AND EXPRESSION CASSETTES AND THEIR USE

(71) Applicant: THE UNIVERSITY OF NORTH CAROLINA AT CHAPEL HILL, Chapel Hill, NC (US)

(72) Inventors: Steven James Gray, Southlake, TX (US); Rachel Bailey, Trophy Club, TX (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 998 days.

(21) Appl. No.: 17/290,927

(22) PCT Filed: Nov. 5, 2019

(86) PCT No.: PCT/US2019/059752
§ 371 (c)(1),
(2) Date: May 3, 2021

(87) PCT Pub. No.: WO2020/097002
PCT Pub. Date: May 14, 2020

(65) Prior Publication Data
US 2021/0371837 A1    Dec. 2, 2021

Related U.S. Application Data

(60) Provisional application No. 62/755,871, filed on Nov. 5, 2018.

(51) Int. Cl.
| | | |
|---|---|---|
| *C12N 9/16* | (2006.01) | |
| *A61K 9/00* | (2006.01) | |
| *A61K 38/46* | (2006.01) | |
| *A61P 21/00* | (2006.01) | |
| *A61P 25/00* | (2006.01) | |
| *C12N 15/86* | (2006.01) | |
| *A61K 48/00* | (2006.01) | |

(52) U.S. Cl.
CPC .............. *C12N 9/16* (2013.01); *A61K 9/0085* (2013.01); *A61K 38/465* (2013.01); *A61P 21/00* (2018.01); *A61P 25/00* (2018.01); *C12N 15/86* (2013.01); *C12Y 301/03036* (2013.01); *A61K 48/00* (2013.01); *C12N 2750/14143* (2013.01); *C12N 2800/22* (2013.01)

(58) Field of Classification Search
None
See application file for complete search history.

(56) References Cited

U.S. PATENT DOCUMENTS

| | | |
|---|---|---|
| 4,501,729 A | 2/1985 | Boucher et al. |
| 5,399,346 A | 3/1995 | Anderson et al. |
| 5,478,745 A | 12/1995 | Samulski et al. |
| 6,040,183 A | 3/2000 | Ferrari et al. |
| 6,093,570 A | 7/2000 | Ferrari et al. |
| 6,156,303 A | 12/2000 | Russell et al. |
| 7,201,898 B2 | 4/2007 | Monahan et al. |
| 9,636,370 B2 | 5/2017 | McCown et al. |
| 10,260,100 B2 * | 4/2019 | Meisler ................ C12Q 1/6883 |
| 2010/0014255 A1 | 1/2010 | Watanabe |
| 2010/0143255 A1 | 6/2010 | Meisler et al. |
| 2016/0304883 A1 | 10/2016 | Grund et al. |
| 2017/0360960 A1 | 12/2017 | Gray et al. |

FOREIGN PATENT DOCUMENTS

| | | |
|---|---|---|
| JP | 2017121241 A | 7/2017 |
| WO | 9811244 A2 | 3/1998 |
| WO | 9961601 A2 | 12/1999 |
| WO | 0017377 A2 | 3/2000 |
| WO | 0028004 A1 | 5/2000 |
| WO | 0028061 A2 | 5/2000 |
| WO | 0191803 A2 | 12/2001 |
| WO | 0192551 A2 | 12/2001 |
| WO | 2009111704 A2 | 9/2009 |
| WO | 2013151663 A1 | 10/2013 |
| WO | 2017136536 A1 | 8/2017 |
| WO | 2017191274 A2 | 11/2017 |

OTHER PUBLICATIONS

Dumont, et al. (2016) "Human cell lines for biopharmaceutical manufacturing: history, status, and future perspectives", Critical Reviews in Biotechnology, 36(6): 1110-1122. (Year: 2016).*
Hamdan, et al. (2002) "Codon optimization improves heterologous expression of Schistosoma mansoni cDNA in HEK293 cell", Parasitology Research, 88: 583-86. (Year: 2002).*
Chahal, et al. (2013) "Production of adeno-associated virus (AAV) serotypes by transient transfection of HEK293 cell suspension cultures for gene delivery", Journal of Virological Methods, 196: 163-73. (Year: 2013).*
Zhou, et al. (2008) "Adeno-associated Virus of a Single-polarity DNA Genome Is Capable of Transduction In Vivo", Molecular Therapy, 16(3): 494-99. (Year: 2008).*
Chow, et al. (2009) "Deleterious Variants of FIG4, a Phosphoinositide Phosphatase, in Patients with ALS", The American Journal of Human Genetics, 84: 85-88. (Year: 2009).*
Presa, et al. (2021) "AAV9-mediated FIG4 delivery prolongs life span in Charcot-Marie-Tooth disease type 4J mouse model", Journal of Clinical Investigation, 131(11): e137159, 11 pages as printed. (Year: 2021).*

(Continued)

Primary Examiner — Robert M Kelly

(74) Attorney, Agent, or Firm — Myers Bigel, P.A.

(57) ABSTRACT

This invention relates to polynucleotides comprising optimized FIG. 4 open reading frame (ORF) sequences, vectors comprising the same, and methods of using the same for delivery of the ORF to a cell or a subject and to treat disorders associated with aberrant expression of a FIG. 4 gene or aberrant activity of a FIG. 4 gene product in the subject, such as CMT4J.

23 Claims, 11 Drawing Sheets

Specification includes a Sequence Listing.

(56) References Cited

OTHER PUBLICATIONS

Extended European Search Report corresponding to European Patent Application No. 19883228.9 (9 pages) (dated Jul. 11, 2022).
Presa et al. "AAV9-mediated FIG4 delivery prolongs life span in Charcot-Marie-Tooth disease type 4J mouse model" Journal of Clinical Investigation, 131(11):e137159 (2021).
Bantel-Schaal et al. "Human Adeno-Associated Virus Type 5 Is Only Distantly Related to Other Known Primate Helper-Dependent Parvoviruses" Journal of Virology, 73(2):939-947 (1999).
Chao et al. "Several Log Increase in Therapeutic Transgene Delivery by Distinct Adeno-Associated Viral Serotype Vectors" Molecular Therapy, 2(6):619-623 (2000).
Chiorini et al. "Cloning and Characterization of Adeno-Associated Virus Type 5" Journal of Virology, 73(2):1309-1319 (1999).
Chiorini et al. "Cloning of Adeno-Associated Virus Type 4 (AAV4) and Generation of Recombinant AAV4 Particles" Journal of Virology, 71(9):6823-6833 (1997).
Chow et al. "Mutation of FIG4 causes neurodegeneration in the pale tremor mouse and patients with CMT4J" Nature, 448:68-72 (2007).
Conway et al. "High-titer recombinant adeno-associated virus production utilizing a recombinant herpes simplex virus type I vector expressing AAV-2 Rep and Cap" Gene Therapy, 6:986-993 (1999).
Dong et al. "PI(3,5)P 2 controls membrane traffi cking by direct activation of mucolipin Ca 2 + release channels in the endolysosome" Nature Communications, 1(38):1-11 (2010).
Ferrari et al. "New developments in the generation of Ad-free, high-titer rAAV gene therapy vectors" Nature Medicine, 3:1295-1297 (1997).
Gao et al. "Novel adeno-associated viruses from rhesus monkeys as vectors for human gene therapy" Proceedings of the National Academy of Sciences USA, 99(18):11854-11859 (2002).
GenBank Accession No. AF028704 "Adeno-associated virus 6, complete genome" www.ncbi.nlm.nih.gov (3 pages) (Jan. 12, 1998).
GenBank Accession No. AF028705 "Adeno-associated virus 3B, complete genome" www.ncbi.nlm.nih.gov (3 pages) (Jan. 12, 1998).
GenBank Accession No. AF043303 "Adeno-associated virus 2, complete genome" www.ncbi.nlm.nih.gov (4 pages) (May 20, 2010).
GenBank Accession No. AF063497 "Adeno-associated virus 1, complete genome" www.ncbi.nlm.nih.gov (3 pages) (Apr. 27, 1999).
GenBank Accession No. AF288061 "Hamster parvovirus 5' terminal hairpin gene sequence" www.ncbi.nlm.nih.gov (1 page) (Apr. 13, 2001).
GenBank Accession No. AF513851 "Adeno-associated virus 7 nonstructural protein and capsid protein genes, complete cds" www.ncbi.nlm.nih.gov (3 pages) (Sep. 5, 2002).
GenBank Accession No. AF513852 "Adeno-associated virus 8 nonstructural protein and capsid protein genes, complete cds" www.ncbi.nlm.nih.gov (3 pages) (Sep. 5, 2002).
GenBank Accession No. AH009962 "Hamster parvovirus" www.ncbi.nlm.nih.gov (2 pages) (Aug. 25, 2016).
GenBank Accession No. AX753250 "Sequence 5 from Patent EP1310571" www.ncbi.nlm.nih.gov (2 pages) (Jun. 23, 2003).
GenBank Accession No. AY028223 "B19 virus isolate patient_A.1.1 genomic sequence" www.ncbi.nlm.nih.gov (1 page) (Apr. 16, 2001).
GenBank Accession No. AY028226 "B19 virus isolate patient_A.2.1 genomic sequence" www.ncbi.nlm.nih.gov (1 page) (Apr. 16, 2001).
GenBank Accession No. AY530579 "Adeno-associated virus 9 isolate hu. 14 capsid protein VP1 (cap) gene, complete cds" www.ncbi.nlm.nih.gov (2 pages) (Jun. 24, 2004).
GenBank Accession No. AY631966 "Adeno-associated virus 11 nonstructural protein and capsid protein genes, complete cds" www.ncbi.nlm.nih.gov (3 pages) (Nov. 30, 2004).
GenBank Accession No. EU285562 "Adeno-associated virus 13 nonstructural protein and capsid protein genes, complete cds" www.ncbi.nlm.nih.gov (3 pages) (Sep. 23, 2008).
GenBank Accession No. J01901 "Adeno-associated virus 2, complete genome" www.ncbi.nlm.nih.gov (3 pages) (Apr. 27, 1993).
GenBank Accession No. J02275 "Minute virus of mice, complete genome" www.ncbi.nlm.nih.gov (5 pages) (May 22, 1995).
GenBank Accession No. NC_000883 "Human parvovirus B19, complete genome" www.ncbi.nlm.nih.gov (4 pages) (Aug. 13, 2018).
GenBank Accession No. NC_001358 "Parvovirus H1, complete genome" www.ncbi.nlm.nih.gov (3 pages) (Feb. 10, 2015).
GenBank Accession No. NC_001401 "Adeno-associated virus—2, complete genome" www.ncbi.nlm.nih.gov (6 pages) (Aug. 13, 2018).
GenBank Accession No. NC_001510 "Minute virus of mice, complete genome" www.ncbi.nlm.nih.gov (5 pages) (Aug. 13, 2018).
GenBank Accession No. NC_001540 "Bovine parvovirus, complete genome" www.ncbi.nlm.nih.gov (4 pages) (Aug. 13, 2018).
GenBank Accession No. NC_001701 "Goose parvovirus, complete genome" www.ncbi.nlm.nih.gov (4 pages) (Aug. 13, 2018).
GenBank Accession No. NC_001729 "Adeno-associated virus—3, complete genome" www.ncbi.nlm.nih.gov (3 pages) (Aug. 13, 2018).
GenBank Accession No. NC_001829 "Adeno-associated virus—4, complete genome" www.ncbi.nlm.nih.gov (3 pages) (Aug. 13, 2018).
GenBank Accession No. NC_001862 "Adeno-associated virus 6, complete genome" www.ncbi.nlm.nih.gov (3 pages) (Jan. 12, 2004).
GenBank Accession No. NC_001863 "Adeno-associated virus 3B, complete genome" www.ncbi.nlm.nih.gov (3 pages) (Jan. 12, 2004).
GenBank Accession No. NC_002077 "Adeno-associated virus—1, complete genome" www.ncbi.nlm.nih.gov (3 pages) (Aug. 13, 2018).
GenBank Accession No. NC_006152 "Adeno-associated virus 5, complete genome" www.ncbi.nlm.nih.gov (3 pages) (Aug. 13, 2018).
GenBank Accession No. NC_006261 "Adeno-associated virus—8, complete genome" www.ncbi.nlm.nih.gov (3 pages) (Aug. 13, 2018).
GenBank Accession No. U89790 "Adeno-associated virus 4, complete genome" www.ncbi.nlm.nih.gov (3 pages) (Aug. 21, 1997).
GenBank Accession No. X01457 "Parvovirus h-1, complete genome" www.ncbi.nlm.nih.gov (3 pages) (Apr. 18, 2005).
Goncalves, Manuel "Adeno-associated virus: from defective virus to effective vector" Virology Journal, 2(43):1-17 (2005).
Gray et al. "Optimizing Promoters for Recombinant Adeno-Associated Virus-Mediated Gene Expression in the Peripheral and Central Nervous System Using Self-Complementary Vectors" Human Gene Therapy, 22:1143-1153 (2011).
Guo et al. "Fig4 Expression in the Rodent Nervous System and Its Potential Role in Preventing Abnormal Lysosomal Accumulation" Journal of Neuropathology & Experimental Neurology, 71(1):28-39 (2012).
Hu et al. "Myelin Abnormality in CMT4J Recapitulates Features of Acquired Demyelination" Annals of Neurology, 83(4):756-770 (2018).
Ikonomov et al. "Sac3 Is an Insulin-regulated Phosphatidylinositol 3,5-Bisphosphate Phosphatase" Journal of Biological Chemistry, 284(36):23961-23971 (2009).
Jin et al. "VAC14 nucleates a protein complex essential for the acute interconversion of PI3P and PI(3,5)P2 in yeast and mouse" The EMBO Journal, 27:3221-3234 (2008).
Katona et al. "Distinct pathogenic processes between Fig4-deficient motor and sensory neurons" European Journal of Neuroscience, 33(8):1401-1410 (2011) (Abstract only).
Lenk et al. "Pathogenic Mechanism of the FIG4 Mutation Responsible for Charcot-Marie-Tooth Disease CMT4J" PLoS Genetics, 7(6):e1002104 (2011).
Margolskee, R. F. "Epstein-Barr Virus Based Expression Vectors" Current Topics in Microbiology and Immunology, 158:67-95 (1992).
McCartney et al. "Phosphatidylinositol 3,5-bisphosphate: low abundance, high significance" Bioessays, 36:52-64 (2014).
Mori et al. "Two novel adeno-associated viruses from cynomolgus monkey: pseudotyping characterization of capsid protein" Virology, 330:375-383 (2004).
Muramatsu et al. "Nucleotide Sequencing and Generation of an Infectious Clone of Adeno-Associated Virus 3" Virology, 221(1):208-217 (1996).

(56) References Cited

OTHER PUBLICATIONS

Palombo et al. "Site-Specific Integration in Mammalian Cells Mediated by a New Hybrid Baculovirus-Adeno-Associated Virus Vector" Journal of Virology, 72(6):5025-5034 (1998).
Ruffing et al. "Mutations in the carboxy terminus of adeno-associated virus 2 capsid proteins affect viral infectivity: lack of an RGD integrin-binding motif" Journal of General Virology, 75:3385-3392 (1994).
Rutledge et al. "Infectious Clones and Vectors Derived from Adeno-Associated Virus (AAV) Serotypes Other Than AAV Type 2" Journal of Virology, 72(1):309-319 (1998).
Schmidt et al. "Molecular Characterization of the Heparin-Dependent Transduction Domain on the Capsid of a Novel Adeno-Associated Virus Isolate, AAV(VR-942)" Journal of Virology, 82(17):8911-8916 (2008).
Shade et al. "Nucleotide Sequence and Genome Organization of Human Parvovirus B19 Isolated from the Serum of a Child during Aplastic Crisis" Journal of Virology, 58(3):921-936 (1986).
Srivastava et al. "Nucleotide Sequence and Organization of the Adeno-Associated Virus 2 Genome" Journal of Virology, 45(2):555-564 (1983).
Urabe et al. "Insect Cells as a Factory to Produce Adeno-Associated Virus Type 2 Vectors" Human Gene Therapy, 13:1935-1943 (2002).
Vaccari et al. "Genetic Interaction between MTMR2 and FIG4 Phospholipid Phosphatases Involved in Charcot-Marie-Tooth Neuropathies" PLoS Genetics, 7(10):e1002319 (2011).
Xiao et al. "Gene Therapy Vectors Based on Adeno-Associated Virus Type 1" Journal of Virology, 73(5):3994-4003 (1999).
Zhang et al. "Mutation of FIG4 causes a rapidly progressive, asymmetric neuronal degeneration" Brain, 131:1990-2001 (2008).
Zhang et al. "Recombinant adenovirus expressing adeno-associated virus cap and rep proteins supports production of hightiter recombinant adeno-associated virus" Gene Therapy, 8:704-712 (2001).
Zolotukhin et al. "Recombinant adeno-associated virus purification using novel methods improves infectious titer and yield" Gene Therapy, 6:973-985 (1999).
Zou et al. "Reactivation of Lysosomal Ca2+ Efflux Rescues Abnormal Lysosomal Storage in FIG4-Deficient Cells" The Journal of Neuroscience, 35(17):6801-6812 (2015).
International Preliminary Report on Patentability corresponding to International Patent Application No. PCT/US2019/059752 (10 pages) (dated May 20, 2021).
International Search Report and the Written Opinion of the International Searching Authority corresponding to International Patent Application No. PCT/US2019/059752 (20 pages) (mailed Feb. 25, 2020).
Lutz et al. "Preclinical gene therapy in a mouse model of Charcot-Marie-Tooth disease type 4J" Molecular Genetics and Metabolism, 126(2):S96-S97, poster No. 225 (2019).

\* cited by examiner

FIG. 2

OPTIMIZED FIG4 GENES AND EXPRESSION CASSETTES AND THEIR USE

STATEMENT OF PRIORITY

This patent application is a 35 U.S.C. § 371 national phase application of PCT Application PCT/US2019/059752 filed Nov. 5, 2019, which claims the benefit, under 35 U.S.C. § 119(e), of U.S. Provisional Application No. 62/755,871, filed on Nov. 5, 2018, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-854_ST25.txt, 44,350 bytes in size, generated on Apr. 19, 2021 and filed via EFS-Web, is provided in lieu of a paper copy. This Sequence Listing is hereby incorporated herein by reference into the specification for its disclosures.

FIELD OF THE INVENTION

This invention relates to polynucleotides comprising optimized FIG4 open reading frame (ORF) sequences, vectors comprising the same, and methods of using the same for delivery of the ORF to a cell or a subject and to treat disorders associated with aberrant expression of a FIG4 gene or aberrant activity of a FIG4 gene product in the subject, such as CMT4J.

BACKGROUND OF THE INVENTION

Factor-Induced Gene 4 (FIG4) encodes a polyphosphoinositide phosphatase, also known as phosphatidylinositol 3,5-bisphosphate 5-phosphatase, SAC domain-containing protein 3 (Sac3), or FIG4. Mutations in FIG4 cause the rare autosomal recessive disease Charcot-Marie-Tooth Neuropathy type 4 J (CMT4J), a type of peripheral neuropathy characterized by childhood onset with clumsy gait, limb weakness, and muscle atrophy [Chow et al. 2007 *Nature* 448:68-72]. Presentation and severity of CMT4J can vary, and patients usually display bi-allelic compound heterozygous mutations in FIG4, where one allele is a null mutant and the other allele is a partial-function missense mutation. Yunis-Varon syndrome is a particularly pathogenic variant of CMT4J, usually caused by bi-allelic pathogenic mutations leading to complete loss of FIG4 function.

FIG4 is highly expressed in myelinating cells, particularly Schwann cells, and dorsal root ganglia sensory neurons [Guo et al. 2012 *J. Neuropathol. Exp. Neurol.* 71(1):28-29]. Schwann cells maintain peripheral nerve myelination. There is consistent demyelination of sensory and motor peripheral nerve axons that are observed in CMT4J patients with depleted FIG4 [Hu et al. 2018 *Ann. Neurol.* 83:756-770]. Demyelination is non-uniform and is often associated with slowed conduction velocity, temporal dispersion, a sign of dis-synchrony of motor nerve responses, conduction block in nerve conduction studies of patients and macrophage infiltration in the spinal roots. The findings are suggestive of the development of demyelinating polyneuropathy. Both motor and sensory neurons in mice and CMT4J patients are impacted to varying degree. Humans with CMT4J mainly experience weakness and muscle atrophy but no or minimal sensory symptoms [Guo et al. 2012; Zhang et al. 2008 *Brain* 131(8):1990-2001].

In CMT disorders, phosphoinositide signaling and vesicular trafficking are reported to play a major role [Chow et al 2007; Vaccari et al. 2011 *PLoS Genet.* 7:e1002319; McCartney et al. 2014 *BioEssays* 36:52-64]. Importantly, FIG4 is only functional in complex with two other protein partners Vac14 and FAB1, and this complex regulates the biosynthesis of phosphatidylinositol 3,5-bisphosphate (PI(3,5)$P_2$) [Jin et al. 2008 *EMBO J.* 27:3221-3234; Ikonomov et al. 2009 *J. Biol. Chem.* 284(36):23961-23971]. The commonly found I41T missense mutation in CMT4J is located at the protein interface with Vac14, which leads to its destabilization and proteasome mediated degradation [Lenk et al. 2011 *PLoS Genet.* 7:31002104] (FIG. 1). Loss of FIG4 results in a drop in the PI(3,5)$P_2$ levels [Chow et al 2007; Katona et al. 2011 *Eur. J. Neurosci.* 33(8):1401-1410]. PI3,5$P_2$ levels are critical for vesicular trafficking and FIG4−/− mice have decreased levels [11] manifesting as excessive lysosomal storage [Katona et al. 2011]. PI(3,5)$P_2$ act as gate keepers for $Ca^{++}$ channels in lysosomal membranes [Dong et al. 2010 *Nat. Commun.* 1:38]. In FIG4−/− cells the $Ca^{++}$ channel deactivation impairs lysosomal fission, including Schwann cells that perform myelination of axons [Zou et al. 2015 *J Neurosci.* 35:6801-6812].

A recent study in European patients has shown that there were 5 amino acid residues in FIG4 that were highly or very highly conserved between human and species as diverse as yeast, round worm (*Caenorhabditis elegans*), fruit fly, chicken, mouse, rat, dog, macaque, orangutan and chimps [McCartney et al. 2014 *BioEssays* 36:52-64]. Patients with FIG4 mutations in these amino acid residues had predominantly upper motor neuronal deficits in some cases there was a rapid progression and lower motor neuronal impact.

Current treatment for CMT4J is limited to symptomatic palliative care, and there remains a need in the art for an effective treatment that targets the cause of the disease. The present invention overcomes shortcomings in the art by providing codon-optimized FIG4 genes, expression cassettes, and vectors capable of providing therapeutic levels of FIG4 expression for treating disorders associated with FIG4 expression such as CMT4J.

SUMMARY OF THE INVENTION

The present invention is based, in part, on the development of optimized FIG4 genes, expression cassettes, and vectors capable of providing therapeutic levels of FIG4 expression for treating disorders associated with FIG4 expression such as CMT4J.

Thus, one aspect of the invention relates to a polynucleotide comprising a human FIG4 open reading frame, wherein the human FIG4 open reading frame has been codon-optimized for expression in human cells.

A further aspect of the invention relates to an expression cassette comprising a polynucleotide comprising a human FIG4 open reading frame and vectors, transformed cells, and transgenic animals comprising the polynucleotide of the invention.

Another aspect of the invention relates to a pharmaceutical formulation comprising the polynucleotide, expression cassette, vector, and/or transformed cell of the invention in a pharmaceutically acceptable carrier.

An additional aspect of the invention relates to a method of expressing a FIG4 open reading frame in a cell, comprising contacting the cell with the polynucleotide, expression cassette, and/or vector of the invention, thereby expressing the FIG4 open reading frame in the cell.

A further aspect of the invention relates to a method of expressing a FIG4 open reading frame in a subject, comprising delivering to the subject the polynucleotide, expression cassette, vector, and/or transformed cell of the invention, thereby expressing the FIG4 open reading frame in the subject.

An additional aspect of the invention relates to a method of treating a disorder associated with aberrant expression of an FIG4 gene or aberrant activity of an FIG4 gene product in a subject in need thereof, comprising administering to the subject a therapeutically effective amount of the polynucleotide, expression cassette, vector, and/or transformed cell of the invention, such that the FIG4 open reading frame is expressed in the subject.

A further aspect of the invention relates to a method of treating Charcot-Marie-Tooth Neuropathy Type 4 J in a subject in need thereof, comprising administering to the subject a therapeutically effective amount of the polynucleotide, expression cassette, vector, and/or transformed cell of the invention, such that the FIG4 open reading frame is expressed in the subject.

Another aspect of the invention relates to a method of treating Yunis-Varon syndrome in a subject in need thereof, comprising administering to the subject a therapeutically effective amount of the polynucleotide, expression cassette, vector, and/or transformed cell of the invention, such that the FIG4 open reading frame is expressed in the subject.

An additional aspect of the invention relates to a method of treating amyotrophic lateral sclerosis in a subject in need thereof, comprising administering to the subject a therapeutically effective amount of the polynucleotide, expression cassette, vector, and/or transformed cell of the invention, such that the FIG4 open reading frame is expressed in the subject.

A further aspect of the invention relates to a method of treating pediatric-onset multiple sclerosis in a subject in need thereof, comprising administering to the subject a therapeutically effective amount of the polynucleotide, expression cassette, vector, and/or transformed cell of the invention, such that the FIG4 open reading frame is expressed in the subject.

Another aspect of the invention relates to a polynucleotide, expression cassette, vector, and/or transformed cell of the invention for use in a method of treating a disorder associated with aberrant expression of a FIG4 gene or aberrant activity of a FIG4 gene product in a subject in need thereof.

These and other aspects of the invention are set forth in more detail in the description of the invention below.

BRIEF DESCRIPTION OF THE DRAWINGS

FIG. 2 shows similarities in FIG4 protein sequence between species. Compared to human (homo) FIG4 protein (SEQ ID NO:7) the mouse (mus; 95.15%; SEQ ID NO:9), rat (*rattus*; 93.94%; SEQ ID NO:10) and monkey (*Macaca*; 99.56%; SEQ ID NO:8) homologues retain high level of amino acid identity. The asterisk (*) annotates a fully conserved amino acid residue, colon (:) annotates strongly similar residues and period (.) annotates weakly similar residues. Amino acids that are not conserved are not annotated.

DETAILED DESCRIPTION OF THE INVENTION

Figure 1:
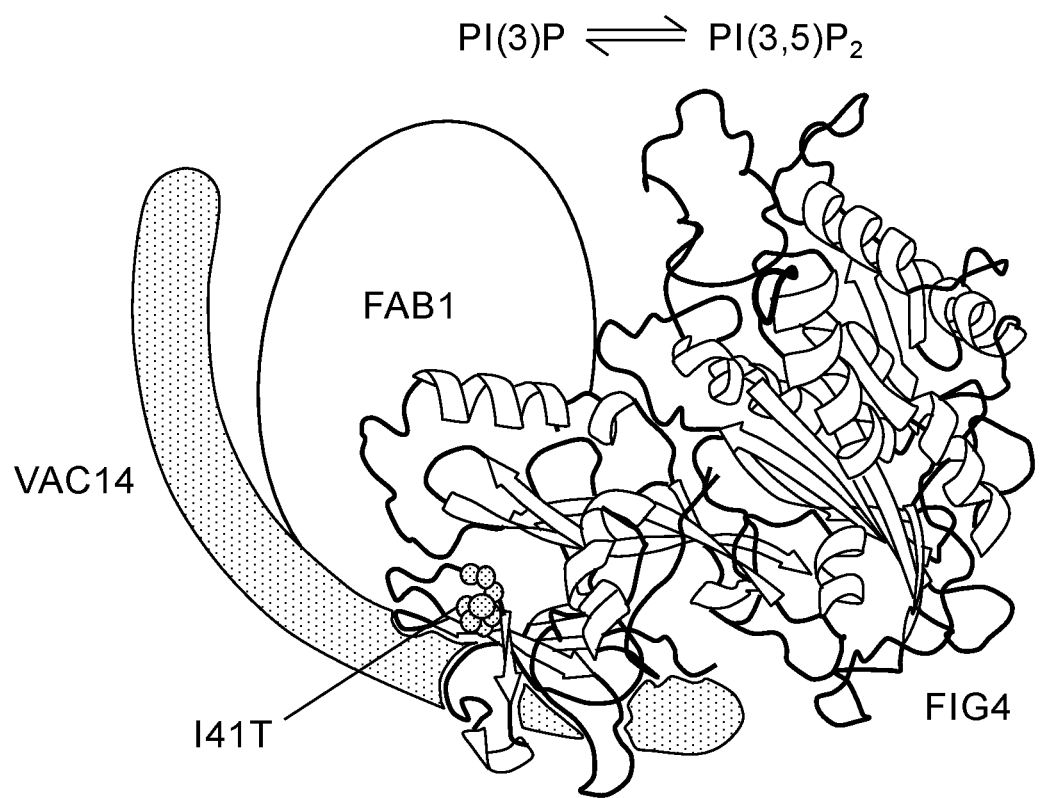
FIG. 1 shows an illustration of the $PI(3,5)P_2$ biosynthesis activity of FIG4 in interaction with protein partners FAB1 and VAC14, and points to the location of the commonly found FIG4 missense mutation I41T.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) *J. Virol.* 78:6381-6388 and Table 1), which are also encompassed by the term "AAV."

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) *Virol.* 33:375-383; Mori et al., (2004) *Virol.* 330:375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

A "chimeric" AAV nucleic acid capsid coding sequence or AAV capsid protein is one that combines portions of two or more capsid sequences. A "chimeric" AAV virion or particle comprises a chimeric AAV capsid protein.

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

The term "tropism profile" refers to the pattern of transduction of one or more target cells, tissues and/or organs. Representative examples of chimeric AAV capsids have a tropism profile characterized by efficient transduction of cells of the central nervous system (CNS) with only low transduction of peripheral organs (see e.g. U.S. Pat. No. 9,636,370 McCown et al., and US patent publication 2017/0360960 Gray et al.).

Figure 4:
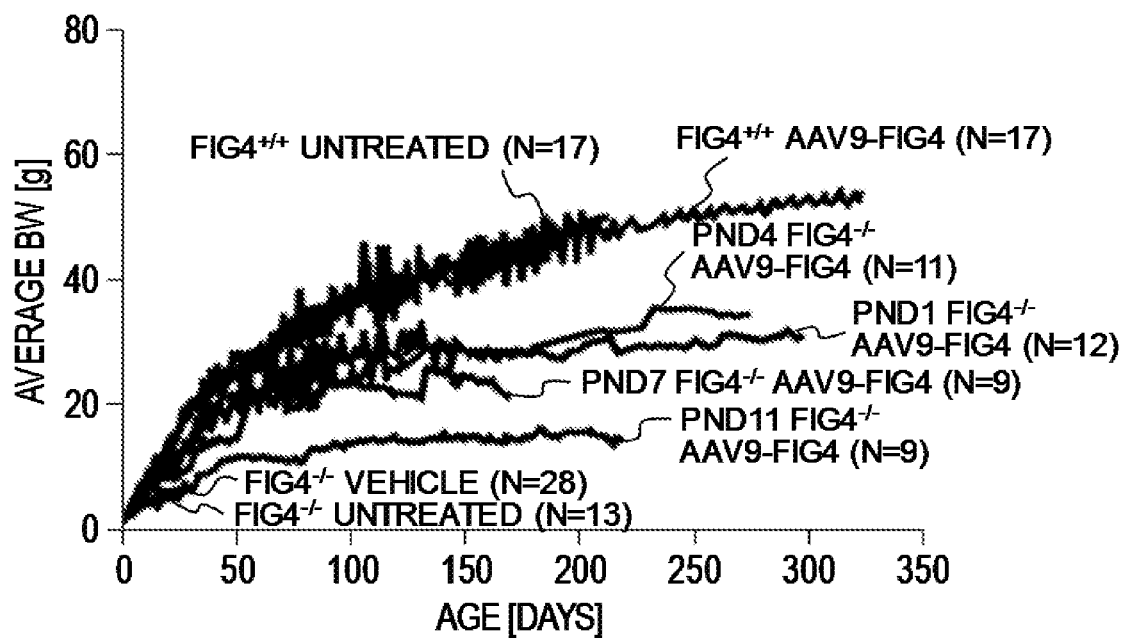
FIG. 4 shows body weight changes. The mice at PND 1 or 4 were dosed ICV (n≥11 per cohort) and PND 7 or 11 were dosed IT (n=9 per cohort). The mean body weights (BW) of each cohort are presented.

The term "disorder associated with aberrant expression of a FIG4 gene" as used herein refers to a disease, disorder, syndrome, or condition that is caused by or a symptom of decreased or altered expression of the FIG4 gene in a subject relative to the expression level in a normal subject or in a population.

The term "disorder associated with aberrant activity of a FIG4 gene product" as used herein refers to a disease, disorder, syndrome, or condition that is caused by or a symptom of decreased or altered activity of the FIG4 gene product in a subject relative to the activity in a normal subject or in a population.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

TABLE 1

| AAV Serotypes/ Isolates | GenBank Accession Number |
|---|---|
| Clonal Isolates | |
| Avian AAV ATCC VR-865 | AY186198, AY629583, NC_004828 |
| Avian AAV strain DA-1 | NC_006263, AY-6.29583 |
| Bovine AAV | NC_005889, AY-3-88617 |
| AAV4 | NC_001829 |
| AAV5 | AY18065, AF085716 |
| Rh34 | AY243001 |
| Rh33 | AY243002 |
| Rh32 | AY243003 |
| AAV10 | AY631965 |
| AAV11 | AY631966 |
| AAV12 | DQ813647 |
| AAV13 | EU285562 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu19 | AY530584 |
| Hu20 | AY530586 |
| Hu23 | AY530589 |

TABLE 1-continued

| AAV Serotypes/Isolates | GenBank Accession Number |
|---|---|
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV 3B | NC_001863 |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| R154 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| AAV9 (Hu14) | AY530579 |
| Hu31 | AY530596 |
| Hu32 | AY530597 |

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) tissues outside the CNS, e.g., liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., CNS cells).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide," "nucleic acid," or "nucleotide sequence" may be of RNA, DNA or DNA-RNA hybrid sequences (including both naturally occurring and non-naturally occurring nucleotides), but is preferably either a single or double stranded DNA sequence.

The term "open reading frame (ORF)," as used herein, refers to the portion of a polynucleotide, e.g., a gene, that encodes a polypeptide.

The term "codon-optimized," as used herein, refers to a gene coding sequence that has been optimized to increase expression by substituting one or more codons normally present in a coding sequence (for example, in a wild-type sequence, including, e.g., a coding sequence for FIG4) with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wild-type gene in an otherwise similar cell.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" (or grammatical equivalents) a virus vector, it is meant that the virus vector is at least partially separated from at least some of the other components in the starting material.

By the term "treat," "treating," or "treatment of" (or grammatically equivalent terms) is meant to reduce or to at least partially improve or ameliorate the severity of the subject's condition and/or to alleviate, mitigate or decrease in at least one clinical symptom and/or to delay the progression of the condition.

As used herein, the term "prevent," "prevents," or "prevention" (and grammatical equivalents thereof) means to delay or inhibit the onset of a disease. The terms are not meant to require complete abolition of disease, and encompasses any type of prophylactic treatment to reduces the incidence of the condition or delays the onset of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

A "heterologous nucleotide sequence" or "heterologous nucleic acid," with respect to a virus, is a sequence or nucleic acid, respectively, that is not naturally occurring in the virus. Generally, the heterologous nucleic acid or nucleotide sequence comprises an open reading frame that encodes a polypeptide and/or a nontranslated RNA.

As used herein, the term "vector," "virus vector," "delivery vector" (and similar terms) in a specific embodiment generally refers to a virus particle that functions as a nucleic acid delivery vehicle, and which comprises the viral nucleic acid (i.e., the vector genome) packaged within the virion. Virus vectors according to the present invention comprise a chimeric AAV capsid according to the invention and can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids, including non-naturally occurring amino acids.

Naturally occurring, levorotatory (L-) amino acids are shown in Table 2.

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 2

|  | Abbreviation | |
| --- | --- | --- |
| Amino Acid Residue | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |

TABLE 2-continued

| | Abbreviation | |
|---|---|---|
| Amino Acid Residue | Three-Letter Code | One-Letter Code |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 3

Amino Acid Residue Derivatives

| Modified Amino Acid Residue | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., (2006) Annu. Rev. Biophys. Biomol. Struct. 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) Human Gene Therapy 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

FIG4 Expression Cassettes and Vectors

The present invention relates to the design of a FIG4 expression cassette to provide therapeutic levels of expression of polyphosphoinositide phosphatase (also known as phosphatidylinositol 3,5-bisphosphate 5-phosphatase, Sac3, or FIG4), the enzyme encoded by the FIG4 gene, and the use of the expression cassette to achieve therapeutic levels of FIG4 in a subject.

Thus, one aspect of the invention relates to a polynucleotide comprising a human FIG4 open reading frame (ORF), wherein the FIG4 open reading frame has been codon-optimized for expression in human cells. The open reading frame is the portion of the FIG4 gene that encodes FIG4. As used herein, a human FIG4 ORF refers to a nucleotide sequence that encodes human FIG4. Codon optimization is a technique well known in the art and optimal codons for expression in humans are known. The use of a codon-optimized FIG4 sequence allows one to distinguish expression of the transduced sequence from expression of the endogenous FIG4 sequence in a subject.

In some embodiments, the codon-optimized FIG4 open reading frame encodes a FIG4 enzyme that is modified from the wild-type sequence, e.g., comprises, consists essentially of, or consists of an amino acid sequence in which 1, 2, 3, 4, or 5 residues have been substituted, added, and/or deleted compared to the wild-type amino acid sequence.

In some embodiments, the codon-optimized FIG4 open reading frame comprises, consists essentially of, or consists of the nucleotide sequence of SEQ ID NO:1 or a sequence at least about 70% identical thereto, e.g., at least about 70, 75, 80, 85, 90, 91, 92, 93, 94, 95, 96, 97, 98, or 99% identical thereto.

```
SEQ ID NO: 1: Human codon-optimized FIG4
open reading frame
ATGCCAACTGCCGCCGCCCCAATCATTTCATCAGTGCAAAAGCTTGTGCT

CTACGAGACAAGAGCTCGGTATTTCCTGGTCGGCTCCAACAACGCAGAAA

CCAAGTACAGAGTGCTTAAGATTGACCGCACCGAACCGAAGGACCTCGTG

ATTATTGACGATCGCCACGTGTACACTCAGCAAGAAGTGCGCGAACTCTT

GGGACGCCTGGACCTGGGCAACCGAACCAAAATGGGCCAGAAGGGCTCCT

CCGGTCTGTTTCGGGCAGTGTCGGCTTTCGGCGTCGTGGGATTCGTGCGA

TTCCTTGAGGGGTACTATATTGTGCTGATCACGAAGCGGCGCAAGATGGC

CGACATCGGAGGACACGCTATATACAAGGTCGAGGACACCAACATGATCT

ACATTCCGAACGATTCAGTCAGAGTGACCCACCCCGATGAAGCCCGCTAC

CTTAGAATCTTCCAGAACGTGGATCTCTCCTCGAACTTTTACTTCTCATA

CTCGTACGACCTGTCCCACTCGCTGCAGTACAACCTGACCGTGCTGCGGA

TGCCTCTGGAGATGCTCAAGTCCGAGATGACTCAAAATCGGCAGGAATCC

TTCGACATCTTCGAGGACGAGGGTCTGATCACTCAAGGAGGGTCGGGAGT

GTTCGGCATTTGCAGCGAACCCTACATGAAATACGTGTGGAACGGAGAGC

TCCTGGACATTATCAAGAGCACTGTGCACCGGGACTGGCTGCTGTACATC

ATCCATGGATTCTGTGGACAGTCAAAGCTCCTGATCTATGGCCGGCCTGT

GTACGTGACTCTGATCGCCCGCCGCTCCTCGAAGTTCGCGGGTACCCGGT

TTCTCAAGCGCGGTGCTAACTGCGAGGGGATGTGGCCAACGAAGTGGAA

ACCGAGCAGATCCTCTGTGACGCCTCCGTGATGAGCTTTACCGCCGGATC

CTACTCTTCGTATGTGCAAGTCCGGGGATCCGTCCCCCTGTACTGGAGCC

AGGACATCTCCACTATGATGCCCAAGCCCCCTATCACCCTGGACCAGGCC

GATCCTTTCGCACACGTGGCTGCCCTGCACTTCGACCAGATGTTCCAGCG

GTTCGGCTCCCCTATCATCATCCTGAACTTGGTCAAGGAACGGGAGAAGC

GGAAGCATGAGAGGATTCTGTCCGAGGAGCTCGTGGCCGCGGTGACCTAC

CTGAATCAGTTCCTCCCGCCCGAACATACCATCGTGTATATCCCCTGGGA

TATGGCCAAGTACACTAAGTCCAAGCTGTGCAATGTGCTGGACCGCCTTA

ACGTCATCGCGGAATCCGTGGTCAAGAAAACCGGATTCTTCGTGAATAGA

CCGGATTCATACTGCTCCATTCTCCGGCCCGATGAAAAGTGGAACGAACT

GGGCGGTTGCGTCATCCCGACTGGCCGGCTCCAGACCGGCATCCTTAGGA

CCAACTGCGTGGACTGCCTGGACAGAACCAACACGGCCCAATTCATGGTC

GGGAAATGTGCCCTGGCCTACCAACTGTACTCCCTGGGACTGATCGACAA

GCCGAACTTGCAATTCGATACTGACGCCGTGCGGCTGTTCGAAGAACTGT

ACGAGGATCACGGCGACACCCTGAGCCTGCAGTACGGCGGAAGCCAGCTC

GTGCATAGAGTGAAAACCTACAGGAAGATTGCTCCGTGGACTCAGCACTC

GAAGGACATCATGCAGACCCTCAGCCGCTACTACTCCAATGCCTTCTCCG

ACGCCGACCGCCAGGACTCCATTAACCTCTTCCTGGGAGTGTTCCACCCA

ACCGAGGGAAAGCCCCACCTGTGGGAACTGCCTACTGATTTCTACTTGCA

TCACAAGAACACCATGAGACTCCTGCCCACCCGGCGCTCCTACACTTACT

GGTGGACCCCTGAAGTGATCAAGCACCTCCCGCTGCCGTACGACGAGGTC

ATCTGCGCCGTGAACCTGAAAAAGCTGATCGTCAAAAAGTTCCATAAATA

TGAAGAAGAAATCGACATTCACAACGAATTCTTCCGGCCATACGAGCTGT

CCTCGTTCGACGACACCTTTTGTCTGGCGATGACCTCATCCGCCCGCGAT

TTCATGCCTAAGACTGTGGGGATCGACCCCAGCCCCTTCACCGTCCGCAA

GCCTGACGAGACTGGAAAGTCGGTGCTCGGCAACAAGAGCAACAGGGAAG

AAGCGGTGCTTCAGAGAAAGACTGCTGCCTCGGCGCCACCGCCGCCTTCC

GAAGAAGCCGTGTCGTCATCCTCGGAAGATGACAGCGGAACCGACCGCGA

GGAGGAGGGGTCCGTGAGCCAGCGGTCCACCCCGGTCAAGATGACTGACG

CCGGGGACTCGGCCAAGGTCACCGAAAACGTGGTGCAACCCATGAAGGAA

CTGTACGGCATCAACCTTAGCGACGGCTTGTCTGAAGAGGACTTCTCCAT
```

```
CTACTCTCGGTTTGTGCAGCTGGGGCAGAGCCAGCACAAGCAGGACAAGA

ATTCCCAACAGCCGTGCAGCAGATGCTCCGACGGAGTGATTAAGCTGACT

CCGATTAGCGCGTTCTCGCAAGATAACATCTACGAAGTGCAACCCCCTCG

CGTGGACAGGAAGTCCACCGAGATTTTCCAGGCCCACATCCAAGCATCCC

AGGGAATCATGCAGCCCCTCGGGAAAGAGGACTCCTCCATGTACCGGGAG

TACATCAGAAACCGCTACCTG
```

Another aspect of the invention relates to an expression cassette comprising a polynucleotide comprising a human FIG4 open reading frame. In certain embodiments, the polynucleotide is a human codon-optimized sequence, e.g., a polynucleotide comprising the nucleotide sequence of SEQ ID NO:1 or a sequence at least about 70% identical thereto, e.g., at least about 70, 75, 80, 85, 90, 91, 92, 93, 94, 95, 96, 97, 98, or 99% identical thereto.

The FIG4 open reading frame in the expression cassette may be operably linked to one or more expression elements that may enhance expression of FIG4. In some embodiments, the polynucleotide is operably linked to a promoter, e.g., a chicken beta-actin promoter, e.g., a promoter comprising, consisting essentially of, or consisting of the nucleotide sequence of SEQ ID NO:2 or a sequence at least about 70% identical thereto, e.g., at least about 70, 75, 80, 85, 90, 91, 92, 93, 94, 95, 96, 97, 98, or 99% identical thereto. In some embodiments, the promoter further comprises the chicken beta-actin exon 1 and intron, e.g., comprising, consisting essentially of, or consisting of the nucleotide sequence of SEQ ID NO:3 or a sequence at least about 70% identical thereto, e.g., at least about 70, 75, 80, 85, 90, 91, 92, 93, 94, 95, 96, 97, 98, or 99% identical thereto.

```
SEQ ID NO: 2: Chicken beta-actin promoter
TACGTATTAGTCATCGCTATTACCATGGTCGAGGTGAGCCCCACGTTCTG

CTTCACTCTCCCCATCTCCCCCCCCTCCCCACCCCCAATTTTGTATTTAT

TTATTTTTTAATTATTTTGTGCAGCGATGGGGGCGGGGGGGGGGGGGGG

CGCGCGCCAGGCGGGGCGGGGCGGGGCGAGGGGCGGGGCGGGGCGAGGCG

GAGAGGTGCGGCGGCAGCCAATCAGAGCGGCGCGCTCCGAAAGTTTCCTT

TTATGGCGAGGCGGCGGCGGCGGCGGCCCTATAAAAAGCGAAGCGCGCGG

CGGGCG

SEQ ID NO: 3: Chicken beta-actin exon 1
and intron
GGAGTCGCTGCGACGCTGCCTTCGCCCCGTGCCCCGCTCCGCCGCCGCCT

CGCGCCGCCCGCCCCGGCTCTGACTGACCGCGTTACTCCCACAGGTGAGC

GGGCGGGACGGCCCTTCTCCTCCGGGCTGTAATTAGCGCTTGGTTTAATG

ACGGCTTGTTTCTTTTCTGTGGCTGCGTGAAAGCCTTGAGGGGCTCCGGG

AGGGCCCTTTGTGCGGGGGGAGCGGCTCGGGGGTGCGTGCGTGTGTGT

GTGCGTGGGGAGCGCCGCGTGCGGCCCGCGCTGCCCGGCGGCTGTGAGCG

CTGCGGGCGCGGCGCGGGGCTTTGTGCGCTCCGCAGTGTGCGCGAGGGGA

GCGCGGCCGGGGCGGTGCCCCGCGGTGCGGGGGGGGCTGCGAGGGGAAC

AAAGGCTGCGTGCGGGGTGTGTGCGTGGGGGGGTGAGCAGGGGGTATGGG

CGCGGCGGTCGGGCTGTAACCCCCCCCTGCACCCCCCTCCCCGAGTTGCT

GAGCACGGCCCGGCTTCGGGTGCGGGGCTCCGTACGGGGCGTGGCGCGGG

GCTCGCCGTGCCGGGCGGGGGTGGCGGCAGGTGGGGGTGCCGGGCGGGG

CGGGGCCGCCTCGGGCCGGGGAGGGCTCGGGGGAGGGGCGCGGCGGCCCC

CGGAGCGCCGGCGGCTGTCGAGGCGCGGCGAGCCGCAGCCATTGCCTTTT

ATGGTAATCGTGCGAGAGGGCGCAGGGACTTCCTTTGTCCCAAATCTGTG

CGGAGCCGAAATCTGGGAGGCGCCGCCGCACCCCCTCTAGCGGGCGCGGG

GCGAAGCGGTGCGGCGCCGGCAGGAAGGAAATGGGCGGGAGGGCCTTCG

TGCGTCGCCGCGCCGCCGTCCCCTTCTCCCTCTCCAGCCTCGGGGCTGTC

CGCGGGGGGACGGCTGCCTTCGGGGGGACGGGGCAGGGCGGGGTTCGGC

TTCTGGCGTGTGACCGGCGGCTCTAGAGCCTCTGCTAACCATGTTCATGC

CTTCTTCTTTTTCCTACAGCTCCTGGGCAACGTGCTGGTTATTGTGCTGT

CTCATCATTTTGGCAAAG
```

In some embodiments, the FIG4 open reading frame is operably linked to an enhancer, e.g., a cytomegalovirus enhancer, e.g., an enhancer comprising, consisting essentially of, or consisting of the nucleotide sequence of SEQ ID NO:4 or a sequence at least about 70% identical thereto, e.g., at least about 70, 75, 80, 85, 90, 91, 92, 93, 94, 95, 96, 97, 98, or 99% identical thereto.

```
SEQ ID NO: 4: Cytomegalovirus enhancer
TGGCCCGCCTGGCTGACCGCCCAACGACCCCCGCCCATTGACGTCAATAG

TAACGCCAATAGGGACTTTCCATTGACGTCAATGGGTGGAGTATTTACGG

TAAACTGCCCACTTGGCAGTACATCAAGTGTATCATATGCCAAGTACGCC

CCCTATTGACGTCAATGACGGTAAATGGCCCGCCTGGCATTATGCCCAGT

ACATGACCTTATGGGACTTTCCTACTTGGCAGTACATCT
```

In some embodiments, the FIG4 open reading frame is operably linked to a polyadenylation signal, e.g., a synthetic polyadenylation signal, e.g., a polyadenylation signal comprising, consisting essentially of, or consisting of the nucleotide sequence of SEQ ID NO:5 or a sequence at least about 70% identical thereto, e.g., at least about 70, 75, 80, 85, 90, 91, 92, 93, 94, 95, 96, 97, 98, or 99% identical thereto.

```
SEQ ID NO: 5: synthetic polyadenylation
signal (SpA)
AATAAAGAGCTCAGATGCATCGATCAGAGTGTGTTGGTTTTTTGTGTG
```

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the FIG4 open reading frame is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

In certain embodiments, the expression cassette further comprises at least one adeno-associated virus (AAV) inverted terminal repeat (ITR), e.g., two AAV ITRs. The two ITRs may have the same nucleotide sequence or different nucleotide sequences. The AAV ITRs may be from any AAV serotype, e.g., AAV2. Each ITR independently may be the wild-type sequence or a modified sequence. In some embodiments, a modified ITR may have a D-element deletion (WO 01/92551). A D-element deletion is defined as the removal of that portion of the ITR known as the D-element. The D-element can be alternatively referred to or known as a D region, or D sequence, and/or the nucleotides of the ITR that do not form palindromic hairpin structures. In some embodiments, the expression cassette is an AAV genome, e.g., a self-complementary AAV genome.

In certain embodiments, the expression cassette comprises an enhancer, a promoter, a human FIG4 open reading frame, and a polyadenylation site, optionally in the recited order. In certain embodiments, the expression cassette comprises an AAV ITR, an enhancer, a promoter, a human FIG4 open reading frame, a polyadenylation site, and an AAV ITR, optionally in the recited order. In certain embodiments, the expression cassette comprises a CMV enhancer, a chicken beta actin promoter, a human FIG4 open reading frame, and a synthetic polyadenylation site, optionally in the recited order. In certain embodiments, the expression cassette comprises a modified AAV ITR, a CMV enhancer, a chicken beta actin promoter, a human FIG4 open reading frame, a synthetic polyadenylation site, and a wild-type AAV ITR, optionally in the recited order. The aforementioned components are in operable linkage.

In some embodiments, the expression cassette comprise, consists essentially of, or consists of the nucleotide sequence of SEQ ID NO:6 or a sequence at least about 70% identical thereto, e.g., at least about 70, 75, 80, 85, 90, 91, 92, 93, 94, 95, 96, 97, 98, or 99% identical thereto.

SEQ ID NO: 6: FIG4 expression cassette
GGGGGGGGGGGGGGGGGTTGGCCACTCCCTCTCTGCGCGCTCGCTCGCTC

ACTGAGGCCGGGCGACCAAAGGTCGCCCGACGCCCGGGCTTTGCCCGGGC

GGCCTCAGTGAGCGAGCGAGCGCGCAGAGAGGGAGTGGCCAACTCCATCA

CTAGGGGTTCCTAGATCTGAATTCGGTACCCGTTACATAACTTACGGTAA

ATGGCCCGCCTGGCTGACCGCCCAACGACCCCCGCCCATTGACGTCAATA

GTAACGCCAATAGGGACTTTCCATTGACGTCAATGGGTGGAGTATTTACG

GTAAACTGCCCACTTGGCAGTACATCAAGTGTATCATATGCCAAGTACGC

CCCCTATTGACGTCAATGACGGTAAATGGCCCGCCTGGCATTATGCCCAG

TACATGACCTTATGGGACTTTCCTACTTGGCAGTACATCTACGTATTAGT

CATCGCTATTACCATGGTCGAGGTGAGCCCCACGTTCTGCTTCACTCTCC

CCATCTCCCCCCCCTCCCCACCCCCAATTTTGTATTTATTTATTTTTTAA

TTATTTTGTGCAGCGATGGGGGCGGGGGGGGGGGGGGGCGCGCGCCAGG

CGGGGCGGGGCGGGGCGAGGGGCGGGGCGGGGCGAGGCGGAAAGGTGCGG

CGGCAGCCAATCAGAGCGGCGCGCTCCGAAAGTTTCCTTTTATGGCGAGG

CGGCGGCGGCGGCGGCCCTATAAAAAGCGAAGCGCGCGGCGGGCGGGAGT

CGCTGCGACGCTGCCTTCGCCCCGTGCCCCGCTCCGCCGCCGCCTCGCGC

CGCCCGCCCCGGCTCTGACTGACCGCGTTACTCCCACAGGTGAGCGGGCG

GGACGGCCCTTCTCCTCCGGGCTGTAATTAGCGCTTGGTTTAATGACGGC

TTGTTTCTTTTCTGTGGCTGCGTGAAAGCCTTGAGGGGCTCCGGGAGGGC

CCTTTGTGCGGGGGGGAGCGGCTCGGGGGGTGCGTGCGTGTGTGTGTGCG

TGGGGAGCGCCGCGTGCGGCCCGCGCTGCCCGGCGGCTGTGAGCGCTGCG

GGCGCGGCGCGGGGCTTTGTGCGCTCCGCAGTGTGCGCGAGGGGAGCGCG

GCCGGGGGCGGTGCCCCGCGGTGCGGGGGGGGCTGCGAGGGGAACAAAGG

CTGCGTGCGGGGTGTGTGCGTGGGGGGGTGAGCAGGGGGTATGGGCGCGG

CGGTCGGGCTGTAACCCCCCCCTGCACCCCCCTCCCCGAGTTGCTGAGCA

CGGCCCGGCTTCGGGTGCGGGGCTCCGTACGGGGCGTGGCGCGGGGCTCG

CCGTGCCGGGCGGGGGTGGCGGCAGGTGGGGGTGCCGGGCGGGGCGGGG

CCGCCTCGGGCCGGGAGGGCTCGGGGGAGGGGCGCGGCGGCCCCCGGAG

CGCCGGCGGCTGTCGAGGCGCGGCGAGCCGCAGCCATTGCCTTTTATGGT

AATCGTGCGAGAGGGCGCAGGGACTTCCTTTGTCCCAAATCTGTGCGGAG

CCGAAATCTGGGAGGCGCCGCCGCACCCCCTCTAGCGGGCGCGGGCGAA

GCGGTGCGGCGCCGGCAGGAAGGAAATGGGCGGGAGGGCCTTCGTGCGT

CGCCGCGCCGCCGTCCCCTTCTCCCTCTCCAGCCTCGGGGCTGTCCGCGG

GGGGACGGCTGCCTTCGGGGGGGACGGGGCAGGGCGGGGTTCGGCTTCTG

GCGTGTGACCGGCGGCTCTAGAGCCTCTGCTAACCATGTTCATGCCTTCT

TCTTTTTCCTACAGCTCCTGGGCAACGTGCTGGTTATTGTGCTGTCTCAT

CATTTTGGCAAAGACCGGTTCCGGACGCCACCATGCCAACTGCCGCCGCC

CCAATCATTTCATCAGTGCAAAAGCTTGTGCTCTACGAGACAAGAGCTCG

GTATTTCCTGGTCGGCTCCAACAACGCAGAAACCAAGTACAGAGTGCTTA

AGATTGACCGCACCGAACCGAAGGACCTCGTGATTATTGACGATCGCCAC

GTGTACACTCAGCAAGAAGTGCGCGAACTCTTGGGACGCCTGGACCTGGG

CAACCGAACCAAAATGGGCCAGAAGGGCTCCTCCGGTCTGTTTCGGGCAG

-continued
TGTCGGCTTTCGGCGTCGTGGGATTCGTGCGATTCCTTGAGGGGTACTAT

ATTGTGCTGATCACGAAGCGGCGCAAGATGGCCGACATCGGAGGACACGC

TATATACAAGGTCGAGGACACCAACATGATCTACATTCCGAACGATTCAG

TCAGAGTGACCCACCCCGATGAAGCCCGCTACCTTAGAATCTTCCAGAAC

GTGGATCTCTCCTCGAACTTTTACTTCTCATACTCGTACGACCTGTCCCA

CTCGCTGCAGTACAACCTGACCGTGCTGCGGATGCCTCTGGAGATGCTCA

AGTCCGAGATGACTCAAAATCGGCAGGAATCCTTCGACATCTTCGAGGAC

GAGGGTCTGATCACTCAAGGAGGGTCGGGAGTGTTCGGCATTTGCAGCGA

ACCCTACATGAAATACGTGTGGAACGGAGAGCTCCTGGACATTATCAAGA

GCACTGTGCACCGGGACTGGCTGCTGTACATCATCCATGGATTCTGTGGA

CAGTCAAAGCTCCTGATCTATGGCCGGCCTGTGTACGTGACTCTGATCGC

CCGCCGCTCCTCGAAGTTCGCGGGTACCCGGTTTCTCAAGCGCGGTGCTA

ACTGCGAGGGGATGTGGCCAACGAAGTGGAAACCGAGCAGATCCTCTGT

GACGCCTCCGTGATGAGCTTTACCGCCGGATCCTACTCTTCGTATGTGCA

AGTCCGGGGATCCGTCCCCCTGTACTGGAGCCAGGACATCTCCACTATGA

TGCCCAAGCCCCCTATCACCCTGGACCAGGCCGATCCTTTCGCACACGTG

GCTGCCCTGCACTTCGACCAGATGTTCCAGCGGTTCGGCTCCCCTATCAT

CATCCTGAACTTGGTCAAGGAACGGGAGAAGCGGAAGCATGAGAGGATTC

TGTCCGAGGAGCTCGTGGCCGCGGTGACCTACCTGAATCAGTTCCTCCCG

CCCGAACATACCATCGTGTATATCCCCTGGGATATGGCCAAGTACACTAA

GTCCAAGCTGTGCAATGTGCTGGACCGCCTTAACGTCATCGCGGAATCCG

TGGTCAAGAAAACCGGATTCTTCGTGAATAGACCGGATTCATACTGCTCC

ATTCTCCGGCCCGATGAAAAGTGGAACGAACTGGGCGGTTGCGTCATCCC

GACTGGCCGGCTCCAGACCGGCATCCTTAGGACCAACTGCGTGGACTGCC

TGGACAGAACCAACACGGCCCAATTCATGGTCGGGAAATGTGCCCTGGCC

TACCAACTGTACTCCCTGGGACTGATCGACAAGCCGAACTTGCAATTCGA

TACTGACGCCGTGCGGCTGTTCGAAGAACTGTACGAGGATCACGGCGACA

CCCTGAGCCTGCAGTACGGCGGAAGCCAGCTCGTGCATAGAGTGAAAACC

TACAGGAAGATTGCTCCGTGGACTCAGCACTCGAAGGACATCATGCAGAC

CCTCAGCCGCTACTACTCCAATGCCTTCTCCGACGCCGACCGCCAGGACT

CCATTAACCTCTTCCTGGGAGTGTTCCACCCAACCGAGGGAAAGCCCCAC

CTGTGGGAACTGCCTACTGATTTCTACTTGCATCACAAGAACACCATGAG

ACTCCTGCCCACCCGGCGCTCCTACACTTACTGGTGGACCCCTGAAGTGA

TCAAGCACCTCCCGCTGCCGTACGACGAGGTCATCTGCGCCGTGAACCTG

AAAAAGCTGATCGTCAAAAAGTTCCATAAATATGAAGAAGAAATCGACAT

TCACAACGAATTCTTCCGGCCATACGAGCTGTCCTCGTTCGACGACACCT

TTTGTCTGGCGATGACCTCATCCGCCCGCGATTTCATGCCTAAGACTGTG

GGGATCGACCCCAGCCCCTTCACCGTCCGCAAGCCTGACGAGACTGGAAA

GTCGGTGCTCGGCAACAAGAGCAACAGGGAAGAAGCGGTGCTTCAGAGAA

AGACTGCTGCCTCGGCGCCACCGCCGCCTTCCGAAGAAGCCGTGTCGTCA

TCCTCGGAAGATGACAGCGGAACCGACCGCGAGGAGGAGGGGTCCGTGAG

-continued
CCAGCGGTCCACCCCGGTCAAGATGACTGACGCCGGGGACTCGGCCAAGG

TCACCGAAAACGTGGTGCAACCCATGAAGGAACTGTACGGCATCAACCTT

AGCGACGGCTTGTCTGAAGAGGACTTCTCCATCTACTCTCGGTTTGTGCA

GCTGGGGCAGAGCCAGCACAAGCAGGACAAGAATTCCCAACAGCCGTGCA

GCAGATGCTCCGACGGAGTGATTAAGCTGACTCCGATTAGCGCGTTCTCG

CAAGATAACATCTACGAAGTGCAACCCCCTCGCGTGGACAGGAAGTCCAC

CGAGATTTTCCAGGCCCACATCCAAGCATCCCAGGGAATCATGCAGCCCC

TCGGGAAAGAGGACTCCTCCATGTACCGGGAGTACATCAGAAACCGCTAC

CTGTAGTAACTCGAGAATAAAGAGCTCAGATGCATCGATCAGAGTGTGTT

GGTTTTTTGTGTGACGCGTGCATGCTGGGGAGAGATCTAGGAACCCCTAG

TGATGGAGTTGGCCACTCCCTCTCTGCGCGCTCGCTCGCTCACTGAGGCC

GCCCGGGCAAAGCCCGGGCGTCGGGCGACCTTTGGTCGCCCGGCCTCAGT

GAGCGAGCGAGCGCGCAGAGAGGGAGTGGCCAACCCCCCCCCCCCCCCC

A further aspect of the invention relates to a vector comprising the polynucleotide or the expression cassette of the invention. Suitable vectors include, but are not limited to, a plasmid, phage, viral vector (e.g., an AAV vector, an adenovirus vector, a herpesvirus vector, an alphavirus vector, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat). In some embodiments, the vector is a delivery vehicle such as a particle (e.g., a microparticle or nanoparticle) or a liposome to which the expression cassette is attached or in which the expression cassette is embedded. The vector may be any delivery vehicle suitable to carry the expression cassette into a cell.

In some embodiments, the vector is a viral vector, e.g., an AAV vector. The AAV vector may be any AAV serotype, e.g., AAV9. In some embodiments, the AAV vector may comprise wild-type capsid proteins. In other embodiments, the AAV vector may comprise a modified capsid protein with altered tropism compared to a wild-type capsid protein, e.g., a modified capsid protein is liver-detargeted or has enhanced tropism for particular cells.

In some embodiments, the vector is a single-stranded AAV (ssAAV) vector. In some embodiments, the vector is a self-complementary or duplexed AAV (scAAV) vector. scAAV vectors are described in international patent publication WO 01/92551 (the disclosure of which is incorporated herein by reference in its entirety). Use of scAAV to express the FIG4 ORF may provide an increase in the number of cells transduced, the copy number per transduced cell, or both.

An additional aspect of the invention relates to a transformed cell comprising the polynucleotide, expression cassette, and/or vector of the invention. In some embodiments, the polynucleotide, expression cassette, and/or vector is stably incorporated into the cell genome. The cell may be an in vitro, ex vivo, or in vivo cell.

Another aspect of the invention relates to a transgenic animal comprising the polynucleotide, expression cassette, vector, and/or the transformed cell of the invention. In some embodiments, the animal is a laboratory animal, e.g., a mouse, rat, rabbit, dog, monkey, or non-human primate.

A further aspect of the invention relates to a pharmaceutical formulation comprising the polynucleotide, expression cassette, vector, and/or transformed cell of the invention in a pharmaceutically acceptable carrier.

In a specific embodiment, the polynucleotide, expression cassette, vector, and/or transformed cell of the invention is isolated.

In another specific embodiment, the polynucleotide, expression cassette, vector, and/or transformed cell of the invention is purified.

Methods of Producing Virus Vectors

The present invention further provides methods of producing virus vectors. In one particular embodiment, the present invention provides a method of producing a recombinant AAV particle, comprising providing to a cell permissive for AAV replication: (a) a recombinant AAV template comprising (i) the polynucleotide or expression cassette of the invention, and (ii) an ITR; (b) a polynucleotide comprising Rep coding sequences and Cap coding sequences; under conditions sufficient for the replication and packaging of the recombinant AAV template; whereby recombinant AAV particles are produced in the cell. Conditions sufficient for the replication and packaging of the recombinant AAV template can be, e.g., the presence of AAV sequences sufficient for replication of the AAV template and encapsidation into AAV capsids (e.g., AAV rep sequences and AAV cap sequences) and helper sequences from adenovirus and/or herpesvirus. In particular embodiments, the AAV template comprises two AAV ITR sequences, which are located 5' and 3' to the polynucleotide of the invention, although they need not be directly contiguous thereto.

In some embodiments, the recombinant AAV template comprises an ITR that is not resolved by Rep to make duplexed AAV vectors as described in international patent publication WO 01/92551.

The AAV template and AAV rep and cap sequences are provided under conditions such that virus vector comprising the AAV template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other Ela trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the Ela or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the AAV rep/cap sequences will not be flanked by the TRs, to prevent rescue and/or packaging of these sequences.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the Ela or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the AAV template is provided by a replicating rAAV virus. In still other embodiments, an AAV provirus comprising the AAV template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV rep/cap sequences and/or the AAV template can be inserted into a deleted region (e.g., the Ela or E3 regions) of the adenovirus.

In a further embodiment, the AAV rep/cap sequences and the adenovirus helper sequences are supplied by a single adenovirus helper vector. According to this embodiment, the AAV template can be provided as a plasmid template.

In another illustrative embodiment, the AAV rep/cap sequences and adenovirus helper sequences are provided by a single adenovirus helper vector, and the AAV template is integrated into the cell as a provirus. Alternatively, the AAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The AAV template can be provided as a separate replicating viral vector. For example, the AAV template can be provided by a AAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by ITRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Ther.* 6:986 and WO 00/17377).

As a further alternative, the virus vectors of the invention can be produced in insect cells using baculovirus vectors to deliver the rep/cap genes and AAV template as described, for example, by Urabe et al., (2002) *Human Gene Ther.* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., ts100K and ts149 adenovirus mutants).

Methods of Using FIG4 Vectors

The present invention also relates to methods for delivering a FIG4 ORF to a cell or a subject to increase production of FIG4, e.g., for therapeutic or research purposes in vitro, ex vivo, or in vivo. Thus, one aspect of the invention relates to a method of expressing a FIG4 open reading frame in a cell, comprising contacting the cell with the polynucleotide, expression cassette, and/or the vector of the invention, thereby expressing the FIG4 open reading frame in the cell. In some embodiments, the cell is an in vitro cell, an ex vivo cell, or an in vivo cell.

Another aspect of the invention relates to a method of expressing a FIG4 open reading frame in a subject, comprising delivering to the subject the polynucleotide, expression cassette, vector, and/or transformed cell of the invention, thereby expressing the FIG4 open reading frame in the subject. In some embodiments, the subject is an animal model of a disorder associated with aberrant FIG4 gene expression.

A further aspect of the invention relates to a method of treating a disorder associated with aberrant expression of a FIG4 gene or aberrant activity of a FIG4 gene product in a subject in need thereof, comprising delivering to the subject a therapeutically effective amount of the polynucleotide, expression cassette, vector, and/or transformed cell of the invention, thereby treating the disorder associated with aberrant expression of the FIG4 gene or aberrant activity of a FIG4 gene product in the subject. The invention provides a method of treating a disorder associated with aberrant expression of a FIG4 gene or aberrant activity of a FIG4 gene product in a subject in need thereof, comprising administering to the subject a therapeutically effective amount of the polynucleotide, the expression cassette, vector, and/or transformed cell of the invention, such that the FIG4 open reading frame is expressed in the subject. In some embodiments, the disorder associated with expression of the FIG4 gene or gene product is CMT4J. In some embodiments, the disorder associated with expression of the FIG4 gene or gene product is Yunis-Varon syndrome. In some embodiments, the disorder associated with expression of the FIG4 gene or gene product is amyotrophic lateral sclerosis. In some embodiments, the disorder associated with expression of the FIG4 gene or gene product is pediatric-onset multiple sclerosis.

The invention further provides a method of treating Charcot-Marie-Tooth Neuropathy Type 4 J in a subject in need thereof, comprising administering to the subject a therapeutically effective amount of the polynucleotide, the expression cassette, vector, and/or transformed cell of the invention, such that the FIG4 open reading frame is expressed in the subject.

The invention further provides a method of treating Yunis-Varon syndrome in a subject in need thereof, comprising administering to the subject a therapeutically effective amount of the polynucleotide, the expression cassette, vector, and/or transformed cell of the invention, such that the FIG4 open reading frame is expressed in the subject.

The invention further provides a method of treating amyotrophic lateral sclerosis in a subject in need thereof, comprising administering to the subject a therapeutically effective amount of the polynucleotide, the expression cassette, vector, and/or transformed cell of the invention, such that the FIG4 open reading frame is expressed in the subject.

The invention further provides a method of treating pediatric-onset multiple sclerosis in a subject in need thereof, comprising administering to the subject a therapeutically effective amount of the polynucleotide, the expression cassette, vector, and/or transformed cell of the invention, such that the FIG4 open reading frame is expressed in the subject.

In certain embodiments, the polynucleotide, expression cassette, vector, and/or transformed cell is delivered to the subject, e.g., systemically (e.g., intravenously) or directly to the central nervous system (e.g., to the cerebrospinal fluid by intrathecal or intraventricular injection) of the subject. In some embodiments, the polynucleotide, expression cassette, vector, and/or transformed cell is delivered intravenously. In some embodiments, the polynucleotide, expression cassette, vector, and/or transformed cell is delivered intracerebroventricularly.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a polynucleotide including those described herein. As a further option, the subject can be a laboratory animal and/or an animal model of disease. Preferably, the subject is a human.

In certain embodiments, the polynucleotide of the invention is administered to a subject in need thereof as early as possible in the life of the subject, e.g., as soon as the subject is diagnosed with aberrant FIG4 expression or activity or any of the above-mentioned diseases or disorders. In some embodiments, the polynucleotide is administered to a newborn subject, e.g., after newborn screening has identified aberrant FIG4 expression or activity. In some embodiments, the polynucleotide is administered to a fetus in utero, e.g., after prenatal screening has identified aberrant FIG4 expression or activity or the presence of one of the above-mentioned diseases or disorders. In some embodiments, the polynucleotide is administered to a subject as soon as the subject develops symptoms associated with aberrant FIG4 expression or activity or is suspected or diagnosed as having aberrant FIG4 expression or activity or one of the above-mentioned diseases or disorders. In some embodiments, the polynucleotide is administered to a subject before the subject develops symptoms associated with aberrant FIG4 expression or activity or disease/disorder, e.g., a subject that is suspected or diagnosed as having aberrant FIG4 expression or activity or one of the above-mentioned diseases or disorders but has not started to exhibit symptoms.

In particular embodiments, the present invention provides a pharmaceutical composition comprising a polynucleotide, expression cassette, vector, and/or transformed cell of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a FIG4 ORF to a cell in vitro. The polynucleotide, expression cassette, and/or vector of the invention may be introduced to the cells in the appropriate amount. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the polynucleotide, expression cassette, and/or vector of the invention, e.g., virus vector, can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

The polynucleotide, expression cassette, and/or vector of the invention, e.g., virus vector, may be introduced to cells in vitro for the purpose of administering the modified cell to a subject. In particular embodiments, the cells have been removed from a subject, the polynucleotide, expression cassette, and/or vector of the invention, e.g., virus vector, is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the polynucleotide, expression cassette, and/or vector of the invention, e.g., virus vector, is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about 103 to about $10^6$ cells will be administered per dose in a pharmaceutically acceptable carrier. In particular embodiments, the cells transduced with the virus vector ex vivo are administered to the subject in an effective amount in combination with a pharmaceutical carrier.

A further aspect of the invention is a method of administering the polynucleotide, expression cassette, and/or vector of the invention, e.g., virus vector, to a subject. In particular embodiments, the method comprises a method of delivering a FIG4 ORF to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$ transducing units or more, e.g., about $10^7$, $10^8$, $10^9$, $10^{10}$, $10^{11}$, $10^{12}$, $10^{13}$, $10^{14}$, or $10^{15}$ transducing units, yet more preferably about $10^{10}$, $10^{11}$, $10^{12}$, $10^{13}$, $10^{14}$, or $10^{15}$ transducing units. Doses and virus titer transducing units may be calculated as vector or viral genomes (vg).

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or a near a tumor or a lymph node). The most suitable route in any given case will depend on the nature and severity of the condition being treated and on the nature of the particular vector that is being used.

In some embodiments, the viral vector is administered to the CNS, the peripheral nervous system, or both.

In some embodiments, the viral vector is administered directly to the CNS, e.g., the brain or the spinal cord. Direct administration can result in high specificity of transduction of CNS cells, e.g., wherein at least 80%, 85%, 90%, 95% or more of the transduced cells are CNS cells. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intranasal, intra-aural, intra-ocular (e.g., intravitreous, sub-retinal, anterior chamber) and peri-ocular (e.g., sub-Tenon's region) delivery or any combination thereof.

The delivery vector may be administered in a manner that produces a more widespread, diffuse transduction of tissues, including the CNS, the peripheral nervous system, and/or other tissues.

Typically, the viral vector will be administered in a liquid formulation by direct injection (e.g., stereotactic injection) to the desired region or compartment in the CNS and/or other tissues. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. Controlled release of parvovirus and AAV vectors is described by international patent publication WO 01/91803.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multidose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 μg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

EXAMPLES

Example 1: Identification of hFIG4opt Efficacy in In Vivo Treatment of FIG4 Deficiency The amino acid sequences of mouse, rat and monkey FIG4 were compared to the optimized human sequence using the Clustal Omega program. The results indicate that FIG4 protein sequence is conserved between species with high-level of amino acid identity (FIG. 2).

The hFIG4 DNA coding sequence of 2721 bp was placed between a 1612 bp chicken beta actin (CBA) promoter with a CMV enhancer and a 48-bp Synthetic polyadenylation (SpA) signal. The CBA promoter and SpA are utilized for their ability to both be small in size as well as drive strong expression allowing for packaging into an AAV vector [Gray et al. 2011 *Hum. Gene Ther.* 22:1143-1153]. The upstream inverted terminal repeat (ITR; proximal to the promoter) is from AAV2, with the D element deleted to promote packaging of a single-stranded (ss) genome. The downstream ITR (proximal to the polyA) is an intact WT AAV2 ITR.

Preclinical studies were conducted in a mouse model lacking FIG4 expression, which recapitulates the recessive human condition. These mice develop motor neuropathy and other aspects of the human disease, and in fact, the identification of the mouse mutation led to the identification of FIG4 as the causative gene for CMT4J. The human and mouse FIG4 proteins and activities are highly conserved, and preclinical studies conducted in the mouse used a codon optimized human FIG4 gene, delivered by AAV9.

The intra-CSF dose was administered to the animals either intracerebroventricularly (ICV) using a ½ cc insulin syringe, or intrathecally (IT) using a Hamilton® syringe. The age of mice at the initiation of the treatment, dose level and route of administration are presented in Table 4.

Treatment at each age included 5 cohorts: 1) Untreated Fig+/+ mice represent a healthy cohort, 2) AAV9/FIG4-injected Fig+/+ mice represent a non-disease phenotype to monitor safety of the gene therapy, 3) AAV9/FIG4-injected FIG4−/− mice to investigate the efficacy and safety of the gene therapy, 4) vehicle administered FIG4−/− mice to represent the natural course of the disease, and 5) untreated FIG4−/− controls mice to monitor any effects from injection technique.

TABLE 4

Preclinical dose administration

| Mice age (weeks) | Route | AAV9/FIG. 4 Dose (vg × $10^{10}$) | Dose volume (μL) |
|---|---|---|---|
| 1* | intracerebroventricular | 54 | 2 |
| 4* | intracerebroventricular | 54 | 2 |
| 7 | Intrathecal | 130.5 | 5 |
| 11 | Intrathecal | 130.5 | 5 |

*Note:
Proof-of-concept cohorts

Figure 3:
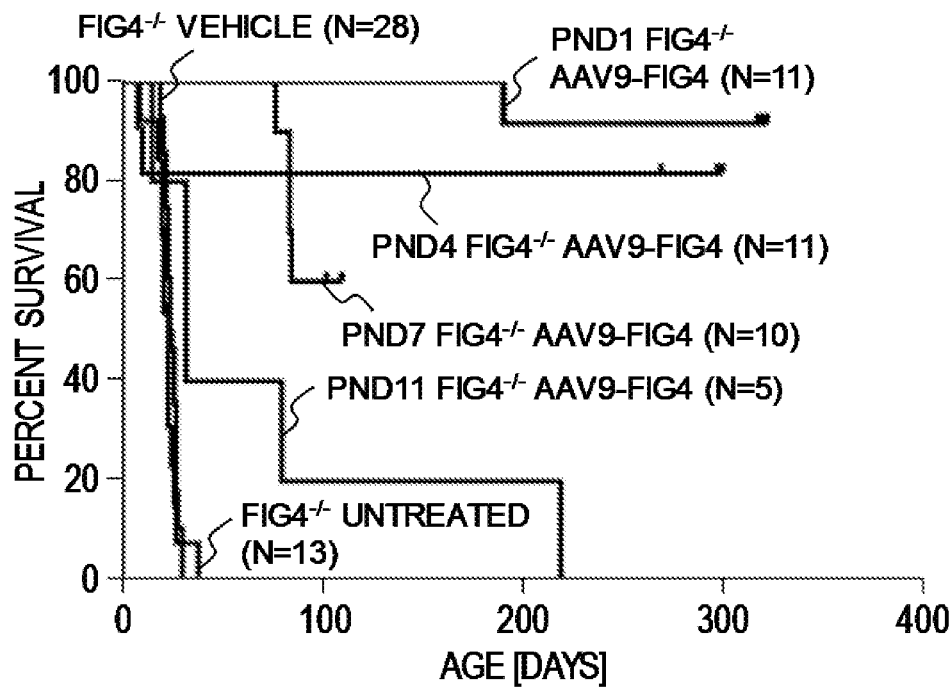
FIG. 3 shows Kaplan-meier survival analysis following AAV9/FIG4 therapy. The mice at Postnatal day 1 (PND1) or 4 (PND4) were dosed intracerebroventricularly (ICV) (n=11 per cohort). Mice at Postnatal days 7 (PND7) or 11 (PND11) were dosed intrathecally (IT) (n≥5 per cohort). The mice were monitored daily for morbidity or mortality. The data are presented as percent survival.
Figure 5:
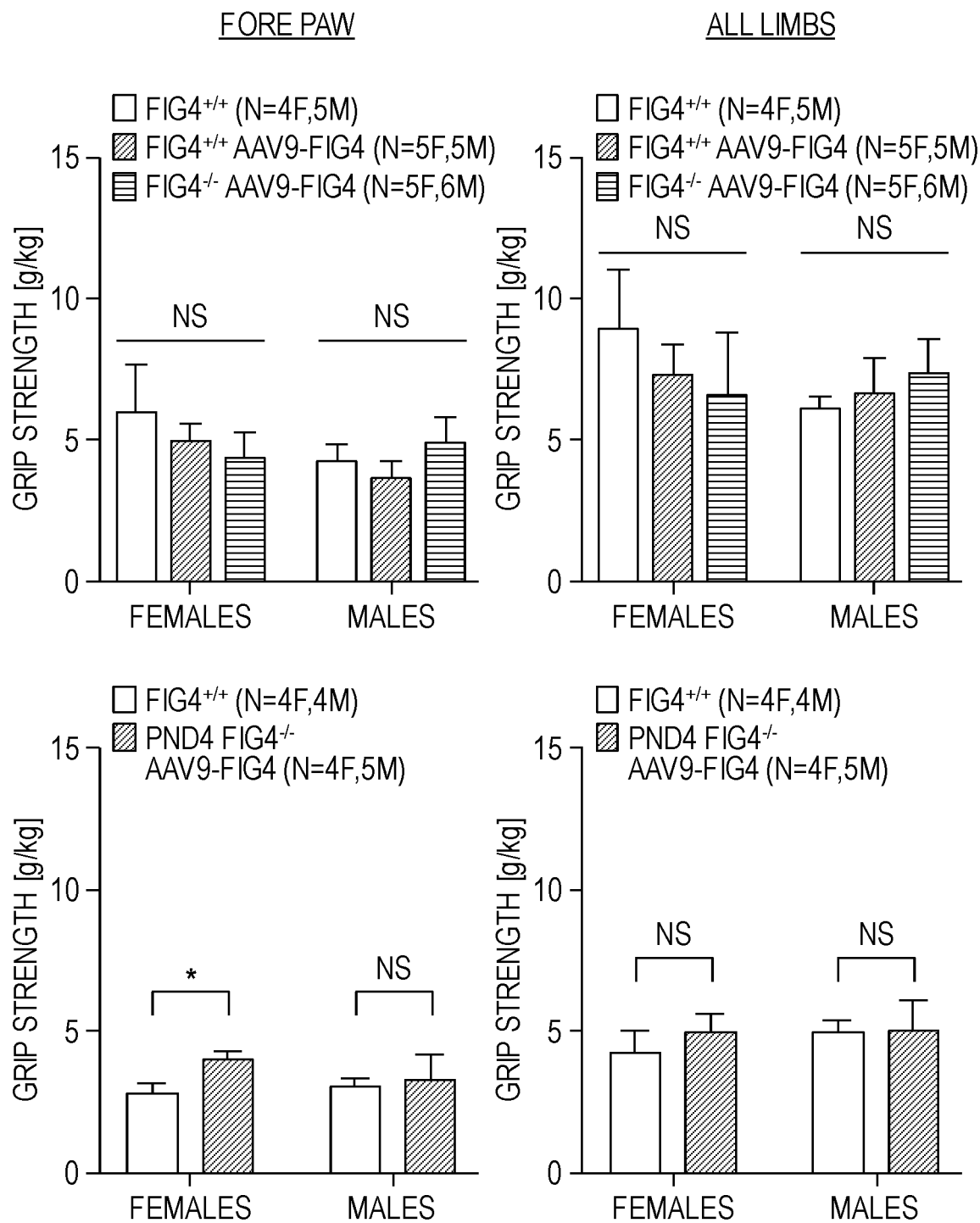
FIG. 5 shows fore arm and all limb grip strength analysis. AAV9/FIG4 therapy improves muscle strength in FIG4−/− mice. The mice at Postnatal day 1 (PND1) or 4 (PND4) were dosed ICV with AAV9-FIG4 (n≥9 per cohort). Upper panels show grip strength assessed in PND1 mice at 2 months old. Lower panels show grip strength assessed in PND4 injected mice at 6 months of age. The mean grip strength normalized to body weight are presented. The data are presented as mean±SD. Mann-Whitney t-test, ns $p>0.05$, *$p<0.05$.
Figure 6:
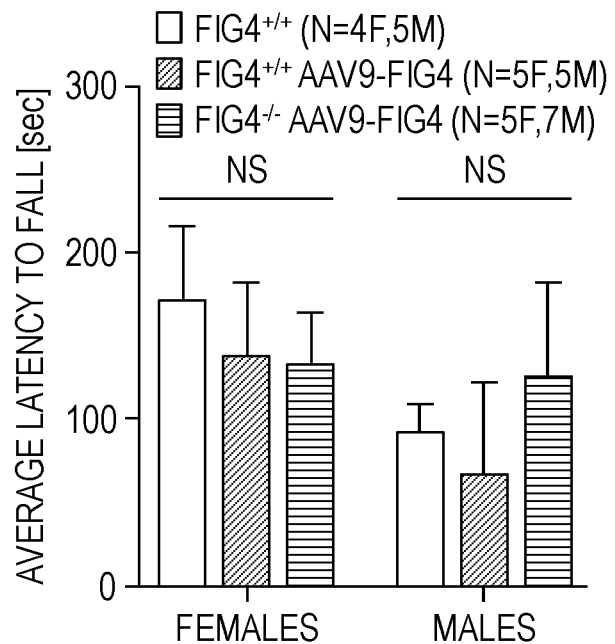
FIG. 6 shows motor coordination analysis. Motor coordination was assessed by rotarod test in PND1 injected mice at 2 months old (upper panel) and in PND4 injected mice at 6 months old (lower panel) (n≥9 per cohort). The graph represents the average latency to fall over 3 trials. The data are presented as mean±SD. Mann-Whitney t-test, ns $p>0.05$.
Figure 6:
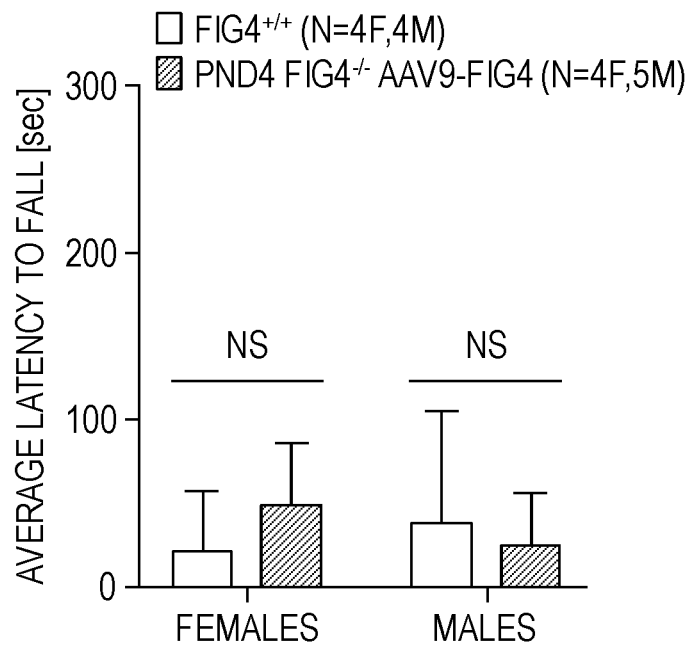
Figure 7:
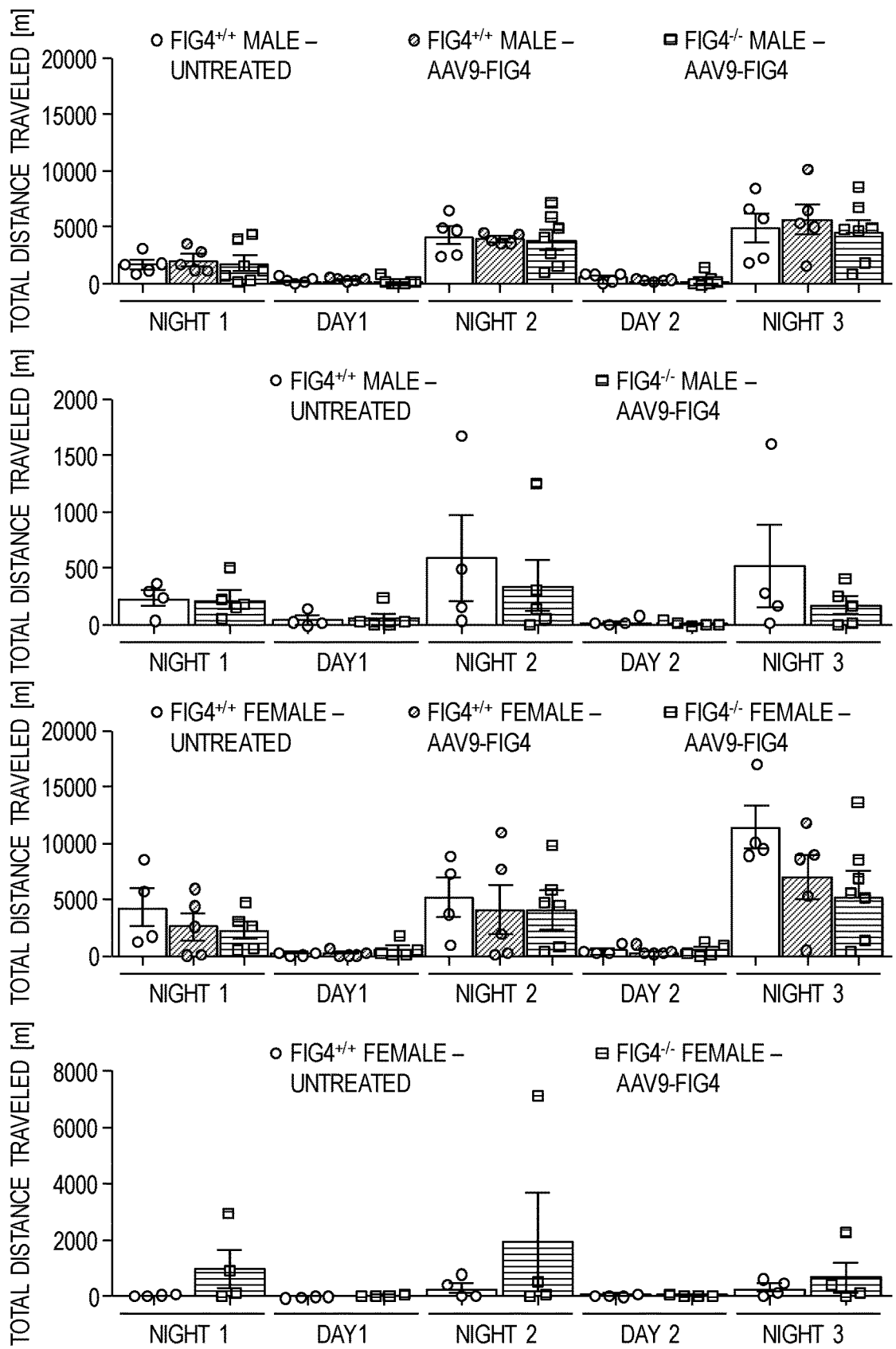
FIG. 7 shows overall activity analysis. Overall activity was tested by spontaneous wheel running during 3 nights. PND1 injected mice (first and third panel) were recorded at 2 months old and PND4 injected mice (second and fourth panel) at 6 months old (n≥9 per cohort). The total distance travelled is presented as mean±SD.
Figure 8:
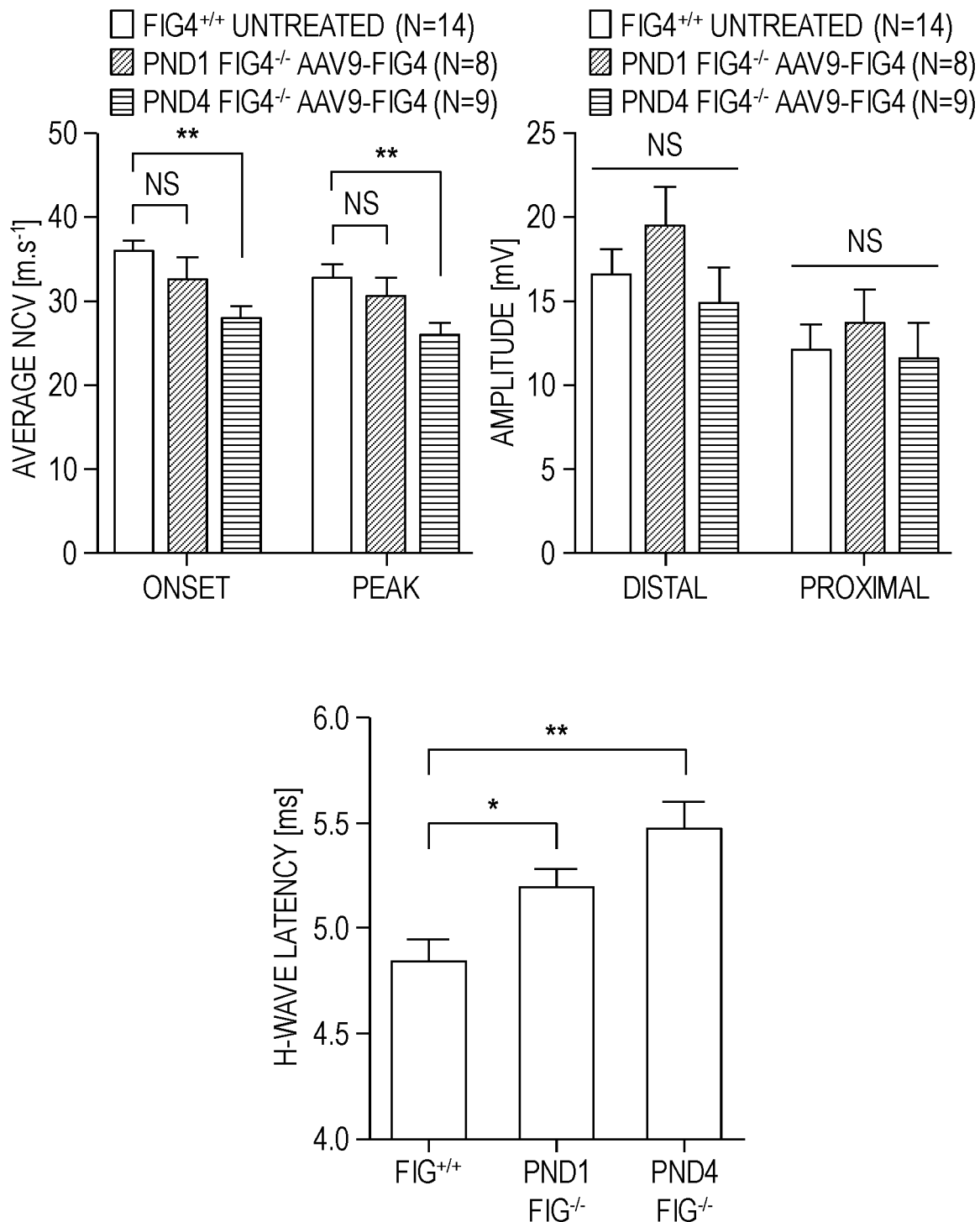
FIG. 8 shows nerve conduction analysis. Nerve conduction velocity was assessed in PND 1 or PND4 ICV-injected mice at 6 months old (n≥8 per cohort). The data are presented as mean±sem. Mann-Whitney t-test, ns $p>0.05$, *$p<0.05$, **$p<0.01$.
Figure 9:
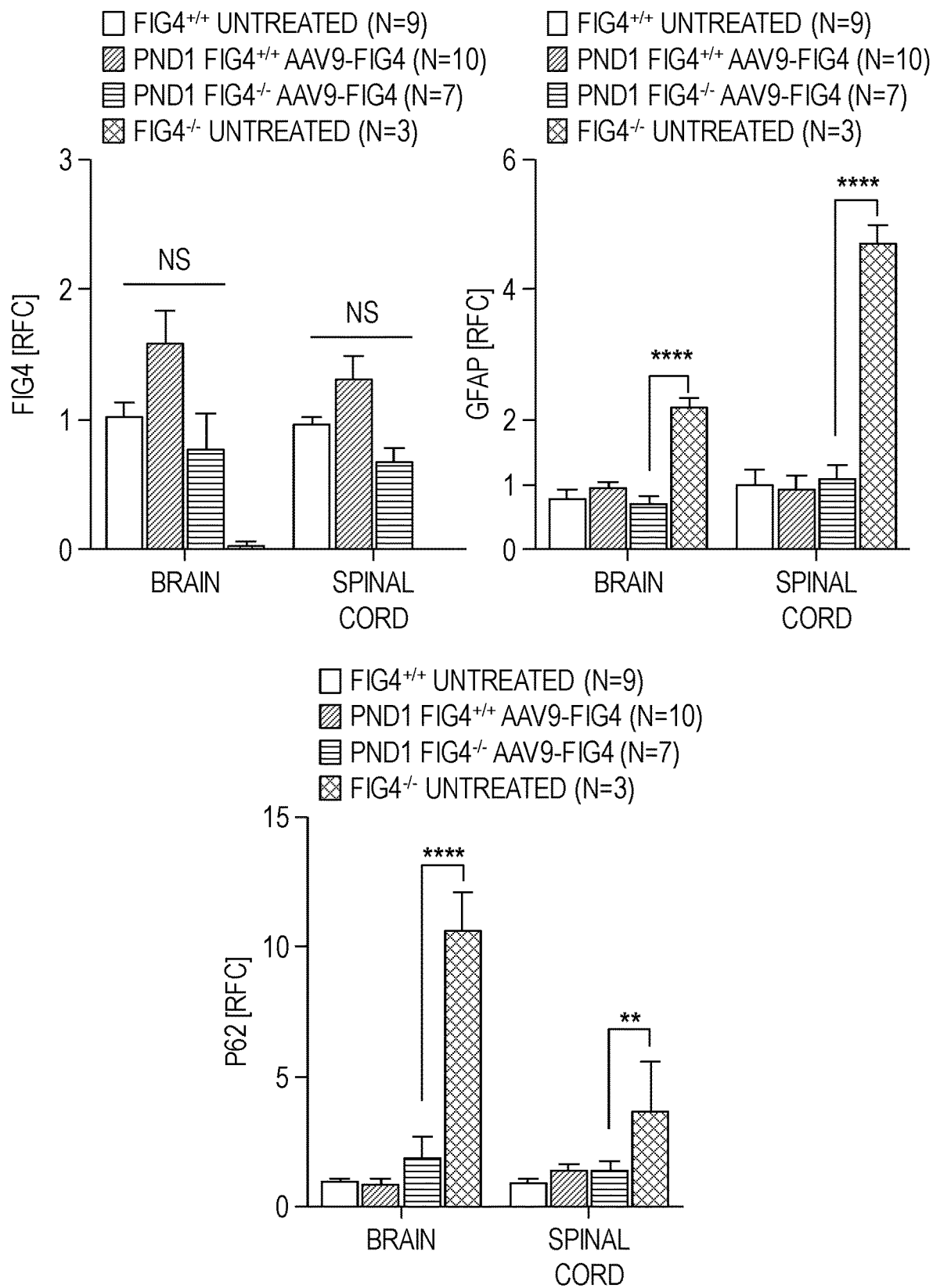
FIG. 9 shows FIG4 protein analysis. Protein levels of FIG4 (left panel), GFAP (central panel) and p62 (right panel) were analyzed by western blot on whole brain and spinal cord of PND1 ICV-injected mice (n≥3 per cohort). The data are presented as mean±sem of the relative fold change (RFC) in each group compared to untreated $FIG4^{+/+}$ mice. Mann-Whitney t-test, ns $p>0.05$, $p<0.01$, **$p<0.0001$.
Figure 10:
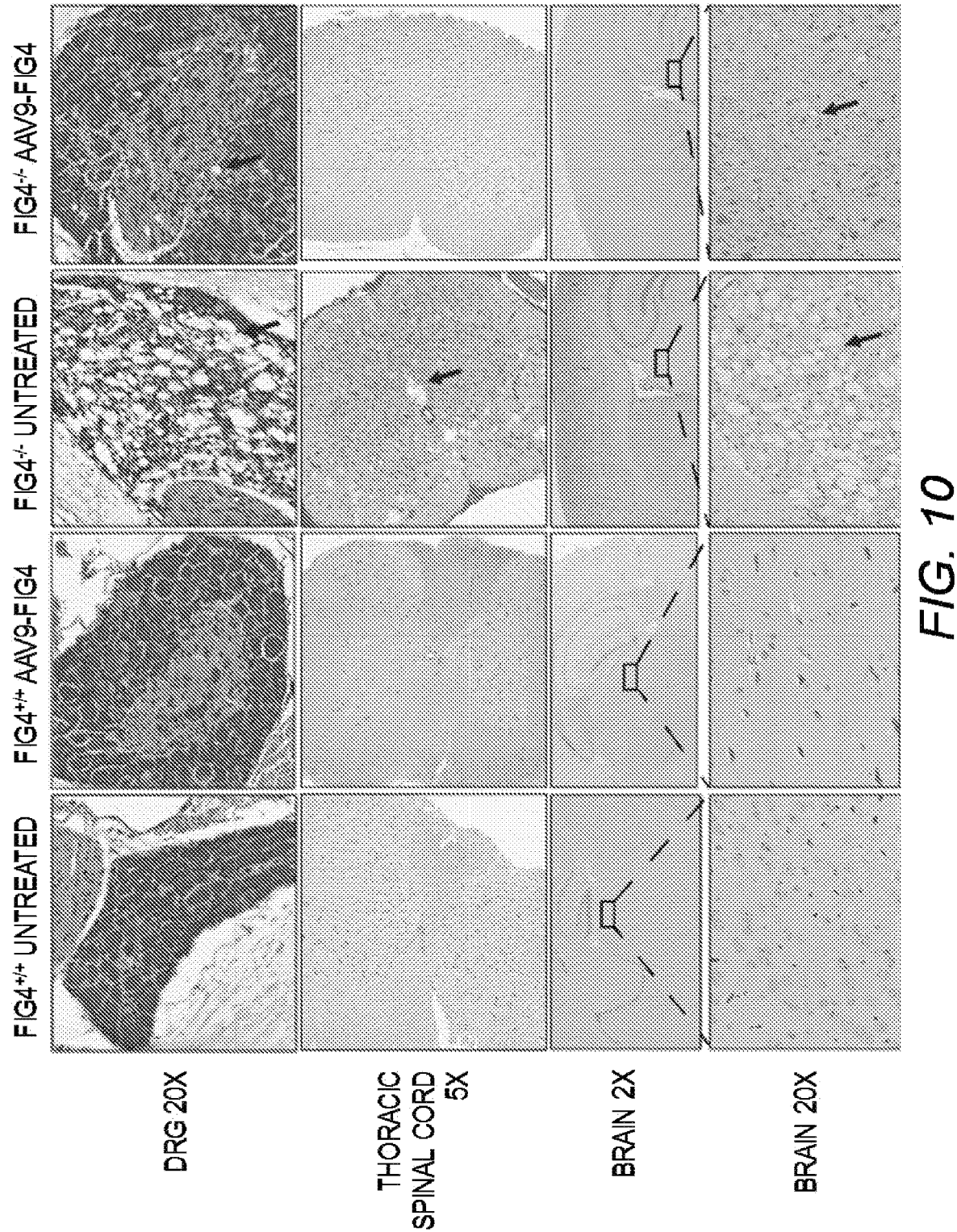
FIG. 10 shows neuropathology in AAV9-FIG4 treated $FIG4^{-/-}$ mice. Dorsal root ganglion (DRG), thoracic spinal cord and brain sections from PND1 ICV-injected mice were stained by H/E. The arrows indicate the presence of cytoplasmic vacuoles.
Figure 11:
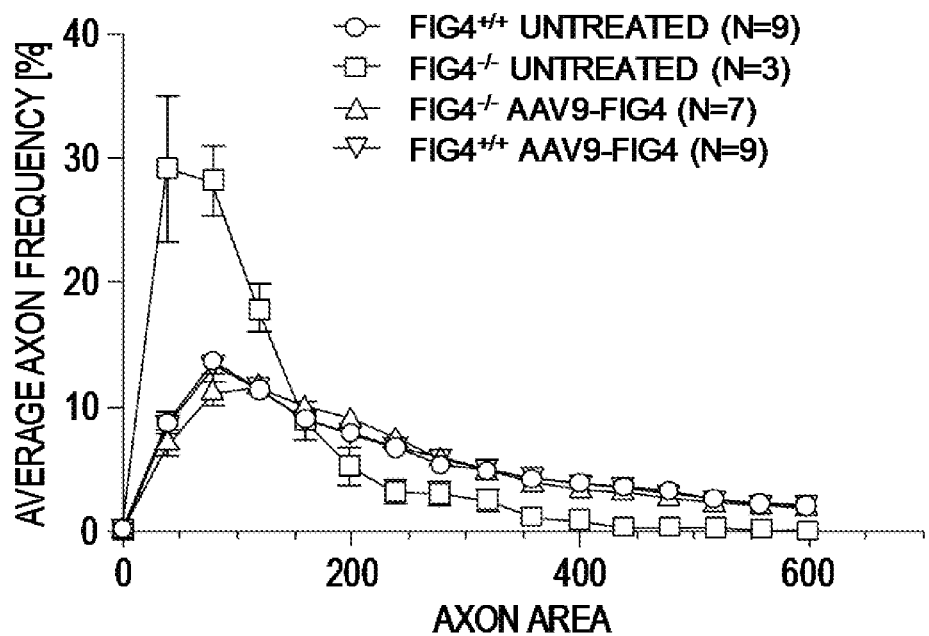
FIG. 11 shows FIG4 nerve histology analysis. Semi-thin sections of sciatic nerve from PND1 ICV-injected mice showed a significant increase in the frequency of large size axons in $FIG4^{-/-}$ treated vs untreated mice. The graph represent the average frequency of axons vs their area. Images are representative semi-thin sections of sciatic nerves analyzed.
Figure 11:
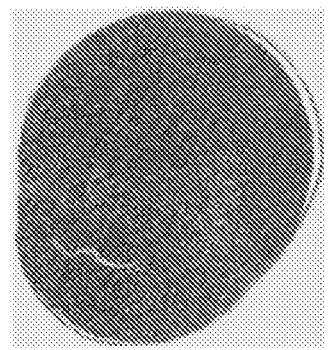
Figure 11:
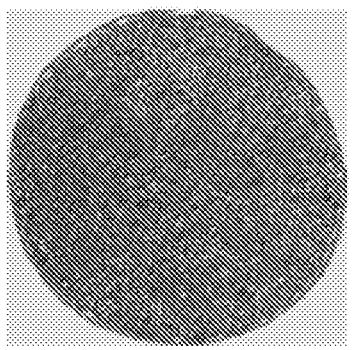
Figure 11:
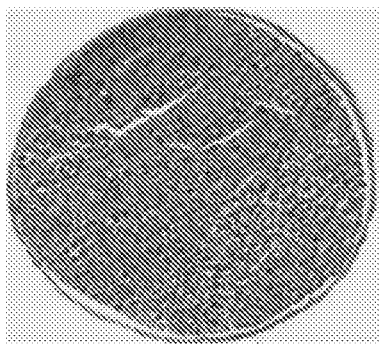
Figure 11:
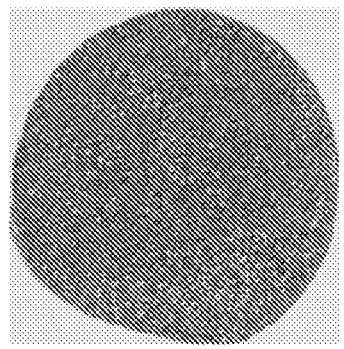
Figure 12:
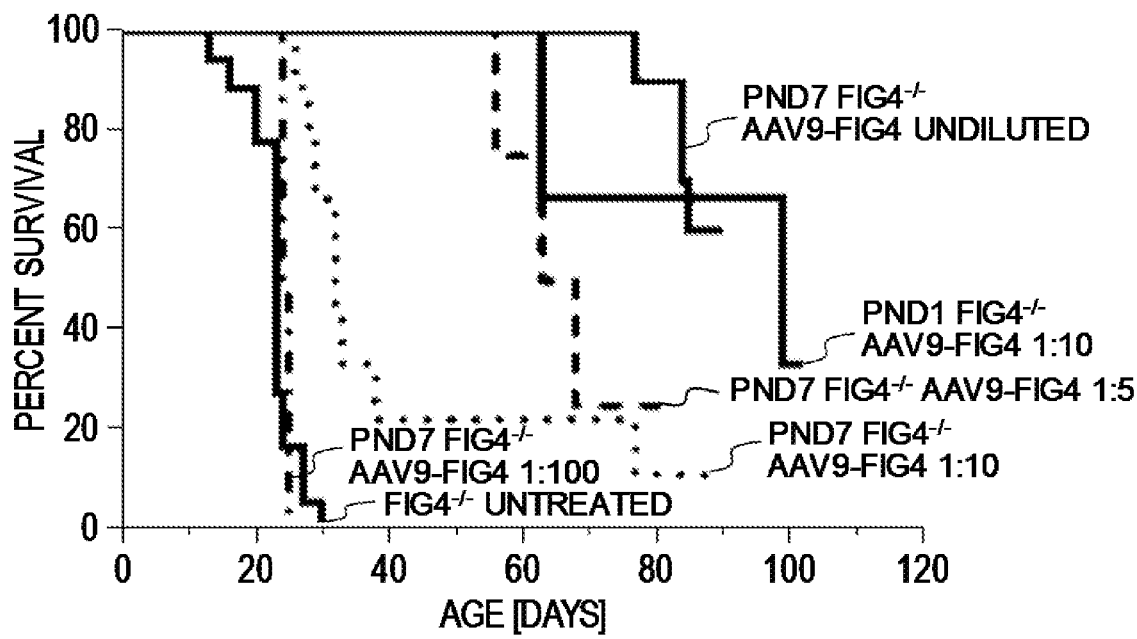
FIG. 12 shows AAV9-FIG4 dose-response analysis. AAV9-FIG4 can rescue FIG4−/− mice in a dose-dependent fashion. PND7 mice were IT (intrathecal) injected with undiluted AAV9-FIG4 ($130.5 \times 10^{10}$ vg) or diluted 1:5, 1:10 and 1:100. PND1 were ICV-injected with AAV9-FIG4 at 1:10 dilution ($5.4 \times 10^{10}$ vg). The mice were monitored daily for morbidity or mortality. The data in the top panel represent the survival analysis (n≥5 per cohort). In the bottom panel, the mean body weights of each cohort are presented.
Figure 12:
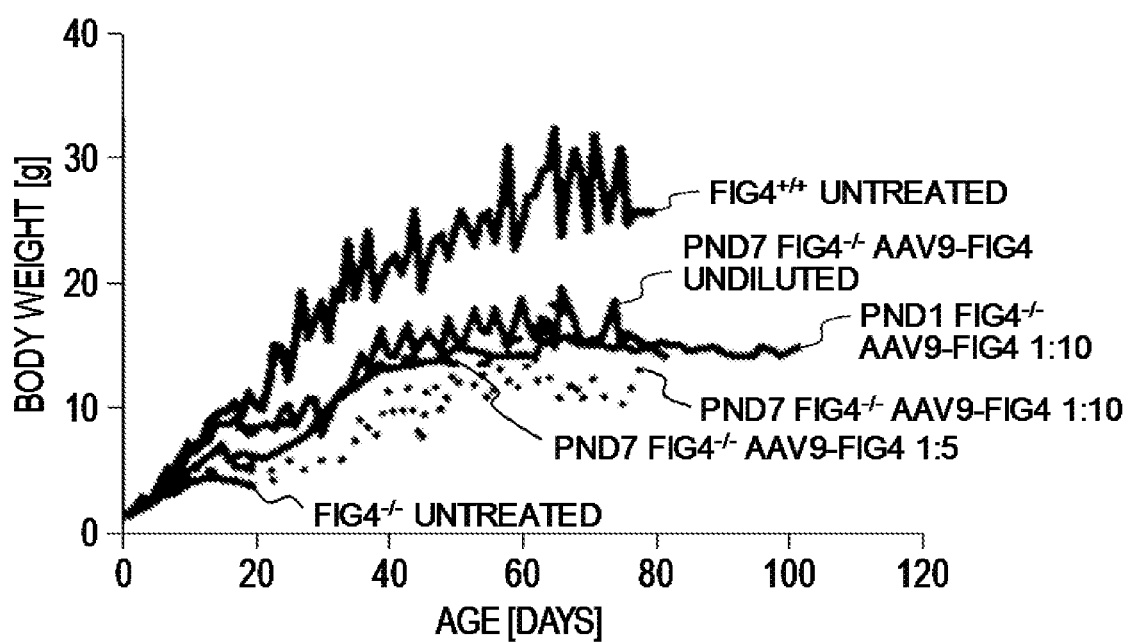

Administering this vector directly to the nervous system by either ICV (P1 and P4) or IT (P7 and P11) injection produced benefit, as indicated by improved survival (FIG. 3), improved gross motor function (FIGS. 6 and 7) including grip strength (FIG. 5), improved peripheral motor nerve conduction (FIG. 8), and improved histopathological outcomes in spinal cord and dorsal root ganglia, as well as other parts of the central nervous system (FIGS. 9, 10, and 11). These outcomes show that the gene replacement is effective in compensating for the FIG4 loss of function mutation. Importantly, our results do indicate that the benefit is greatest the earlier the FIG4-AAV9 is delivered. Our results also indicate a clear dose-response of the treatment up to the maximum feasible dose in P7 mice, justifying the maximum feasible dose to provide the most effective treatment (FIG. 12). In addition, no adverse effects, either overtly or by histopathological examination, were observed in FIG4 mutant or littermate control mice when treated with the vector (FIGS. 3 and 4).

All references cited herein are incorporated herein by reference in their entireties and for all purposes to the same extent as if each individual publication or patent or patent application was specifically and individually indicated to be incorporated by reference in its entirety for all purposes.

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A polynucleotide comprising a human FIG4 open reading frame, wherein the human FIG4 open reading frame is codon-optimized for expression in a human cell, wherein said human FIG4 open reading frame comprises the nucleotide sequence of SEQ ID NO: 1 or a nucleotide sequence having at least about 90% identity thereto.

2. An expression cassette comprising the polynucleotide of claim 1.

3. The expression cassette of claim 2, wherein the human FIG4 open reading frame is operably linked to a promoter, an enhancer, and/or a polyadenylation signal.

4. The expression cassette of claim 3, wherein the promoter is a chicken beta actin promoter, wherein the enhancer is a cytomegalovirus enhancer, and/or wherein the polyadenylation signal is a synthetic polyadenylation signal.

5. The expression cassette of claim 3, further comprising at least one adeno-associated virus (AAV) inverted terminal repeat (ITR).

6. The expression cassette of claim 5, wherein the expression cassette comprises two AAV ITRs.

7. The expression cassette of claim 6, wherein one of the two AAV ITRs is a modified ITR.

8. The expression cassette of claim 6, wherein one of the two AAV ITRs is a D-element deletion modified ITR.

9. The expression cassette of claim 6, wherein the AAV ITRs are AAV2 ITRs.

10. The expression cassette of claim 9, wherein the expression cassette is a self-complementary AAV genome.

11. The expression cassette of claim 2, wherein the expression cassette comprises a promoter, the human FIG4 open reading frame, and a polyadenylation site.

12. The expression cassette of claim 11, wherein the expression cassette comprises an AAV ITR, an enhancer, a promoter, the human FIG4 open reading frame, a polyadenylation site, and an AAV ITR.

13. The expression cassette of any one of claim 12, wherein the expression cassette comprises a CMV enhancer, a chicken beta actin promoter, the human FIG4 open reading frame, and a synthetic polyadenylation site.

14. The expression cassette of claim 13, wherein the expression cassette comprises a modified AAV ITR, a CMV enhancer, a chicken beta actin promoter, the human FIG4 open reading frame, a synthetic polyadenylation site, and a WT AAV ITR.

15. The expression cassette of claim 14, comprising the nucleotide sequence of SEQ ID NO:6 or a sequence at least about 90% identical thereto.

16. A vector comprising the polynucleotide of claim 1.

17. The vector of claim 16, wherein the vector is an AAV vector.

18. The vector of claim 17, wherein the AAV vector is an AAV9 vector.

19. A pharmaceutical composition comprising the vector of claim 17, in a pharmaceutically acceptable carrier.

20. A method of treating Charcot-Marie-Tooth Neuropathy Type 4 J and/or Yunis-Varon syndrome in a subject in need thereof, comprising administering to the subject a therapeutically effective amount of the pharmaceutical composition of claim 19, such that the FIG4 open reading frame is expressed in the subject.

21. The method of claim 20, wherein the subject is a human.

22. The method of claim 20, wherein the pharmaceutical composition is delivered to the nervous system of the subject.

23. The method of claim 22, wherein the pharmaceutical composition is delivered by intrathecal, intracerebral, intracerebroventricular, intranasal, intra-aural, intra-ocular, or peri-ocular delivery, or any combination thereof.

* * * * *

UNITED STATES PATENT AND TRADEMARK OFFICE
CERTIFICATE OF CORRECTION

Page 1 of 3

PATENT NO. : 12,270,057 B2
APPLICATION NO. : 17/290927
DATED : April 8, 2025
INVENTOR(S) : Gray et al.

It is certified that error appears in the above-identified patent and that said Letters Patent is hereby corrected as shown below:

On the Title Page

(57) ABSTRACT: Please delete the abstract and replace with the following:
(57) Abstract: This invention relates to polynucleotides comprising optimized FIG4 open reading frame (ORF) sequences, vectors comprising the same, and methods of using the same for delivery of the ORF to a cell or a subject and to treat disorders associated with aberrant expression of a FIG4 gene or aberrant activity of a FIG4 gene product in the subject, such as CMT4J.

In the Specification

Column 8, TABLE 1: Please delete TABLE 1 and replace with the following:

Signed and Sealed this
Twelfth Day of August, 2025

Coke Morgan Stewart
*Acting Director of the United States Patent and Trademark Office*

Table 1

| AAV Serotypes/Isolates | GenBank Accession Number | AAV Serotypes/Isolates | GenBank Accession Number | AAV Serotypes/Isolates | GenBank Accession Number |
|---|---|---|---|---|---|
| Clonal Isolates | | Hu S17 | AY695376 | Cy3 | AY243019 |
| Avian AAV ATCC VR-865 | AY186198, AY629583, NC_004828 | Hu T88 | AY695375 | Cy5 | AY243017 |
| Avian AAV strain DA-1 | NC_006263, AY629583 | Hu T71 | AY695374 | Rh13 | AY243013 |
| Bovine AAV | NC_005889, AY388617 | Hu T70 | AY695373 | | |
| AAV4 | NC_001829 | Hu T40 | AY695372 | Clade E | |
| AAV5 | AY18065, AF085716 | Hu T32 | AY695371 | Rh38 | AY530558 |
| Rh34 | AY243001 | Hu T17 | AY695370 | Hu66 | AY530626 |
| Rh33 | AY243002 | Hu LG15 | AY695377 | Hu42 | AY530605 |
| Rh32 | AY243003 | | | Hu67 | AY530627 |
| AAV10 | AY631965 | Clade C | | Hu40 | AY530603 |
| AAV11 | AY631966 | AAV 3 | NC_001729 | Hu41 | AY530604 |
| AAV12 | DQ813647 | AAV 3B | NC_001863 | Hu37 | AY530600 |
| AAV13 | EU285562 | Hu9 | AY530629 | Rh40 | AY530559 |
| | | Hu10 | AY530576 | Rh2 | AY243007 |
| Clade A | | Hu11 | AY530577 | Bb1 | AY243023 |
| AAV1 | NC_002077, AF063497 | Hu53 | AY530615 | Bb2 | AY243022 |
| AAV6 | NC_001862 | Hu55 | AY530617 | Rh10 | AY243015 |
| Hu48 | AY530611 | Hu54 | AY530616 | Hu17 | AY530582 |
| Hu43 | AY530606 | Hu7 | AY530628 | Hu6 | AY530621 |
| Hu44 | AY530607 | Hu18 | AY530583 | Rh25 | AY530557 |
| Hu46 | AY530609 | Hu15 | AY530580 | Pi2 | AY530554 |
| | | Hu16 | AY530581 | Pi1 | AY530553 |
| Clade B | | Hu25 | AY530591 | Pi3 | AY530555 |
| Hu19 | AY530584 | Hu60 | AY530622 | Rh57 | AY530569 |
| Hu20 | AY530586 | Ch5 | AY243021 | Rh50 | AY530563 |
| Hu23 | AY530589 | Hu3 | AY530595 | Rh49 | AY530562 |
| Hu22 | AY530588 | Hu1 | AY530575 | Hu39 | AY530601 |
| Hu24 | AY530590 | Hu4 | AY530602 | Rh58 | AY530570 |
| Hu21 | AY530587 | Hu2 | AY530585 | Rh61 | AY530572 |
| Hu27 | AY530592 | Hu61 | AY530623 | Rh52 | AY530565 |
| Hu28 | AY530593 | | | Rh53 | AY530566 |
| Hu29 | AY530594 | Clade D | | Rh51 | AY530564 |
| Hu63 | AY530624 | Rh62 | AY530573 | Rh64 | AY530574 |
| Hu64 | AY530625 | Rh48 | AY530561 | Rh43 | AY530560 |
| Hu13 | AY530578 | Rh54 | AY530567 | AAV8 | AF513852 |
| Hu56 | AY530618 | Rh55 | AY530568 | Rh8 | AY242997 |
| Hu57 | AY530619 | Cy2 | AY243020 | Rh1 | AY530556 |
| Hu49 | AY530612 | AAV7 | AF513851 | | |
| Hu58 | AY530620 | Rh35 | AY243000 | Clade F | |
| Hu34 | AY530598 | Rh37 | AY242998 | AAV9 (Hu14) | AY530579 |
| Hu35 | AY530599 | Rh36 | AY242999 | Hu31 | AY530596 |
| AAV2 | NC_001401 | Cy6 | AY243016 | Hu32 | AY530597 |
| Hu45 | AY530608 | Cy4 | AY243018 | | |
| Hu47 | AY530610 | | | | |
| Hu51 | AY530613 | | | | |
| Hu52 | AY530614 | | | | |
| Hu T41 | AY695378 | | | | |

Column 30, Line 35: Please correct "103" to read --$10^3$--

SEQUENCE LISTING

```
<160> NUMBER OF SEQ ID NOS: 10

<210> SEQ ID NO 1
<211> LENGTH: 2721
<212> TYPE: DNA
<213> ORGANISM: Artificial
<220> FEATURE:
<223> OTHER INFORMATION: Human codon-optimized FIG4 open reading frame

<400> SEQUENCE: 1
atgccaactg ccgccgcccc aatcatttca tcagtgcaaa agcttgtgct ctacgagaca        60
agagctcggt atttcctggt cggctccaac aacgcagaaa ccaagtacag agtgcttaag       120
attgaccgca ccgaaccgaa ggacctcgtg attattgacg atcgccacgt gtacactcag       180
caagaagtgc gcgaactctt gggacgcctg gacctgggca accgaaccaa aatgggccag       240
aagggctcct ccggtctgtt tcgggcagtg tcggctttcg gcgtcgtggg attcgtgcga       300
ttccttgagg ggtactatat tgtgctgatc acgaagcggc gcaagatggc cgacatcgga       360
ggacacgcta tatacaaggt cgaggacacc aacatgatct acattccgaa cgattcagtc       420
agagtgaccc accccgatga agcccgctac cttagaatct tccagaacgt ggatctctcc       480
tcgaactttt acttctcata ctcgtacgac ctgtcccact cgctgcagta caacctgacc       540
gtgctgcgga tgcctctgga gatgctcaag tccgagatga ctcaaaatcg gcaggaatcc       600
ttcgacatct tcgaggacga gggtctgatc actcaaggag ggtcgggagt gttcggcatt       660
tgcagcgaac cctacatgaa atacgtgtgg aacgagagc tcctggacat tatcaagagc       720
actgtgcacc gggactggct gctgtacatc atccatggat tctgtggaca gtcaaagctc       780
ctgatctatg gccggcctgt gtacgtgact ctgatcgccc gccgctcctc gaagttcgcg       840
ggtacccggt ttctcaagcg cggtgctaac tgcgaggggg atgtgccaa cgaagtggaa       900 accgagcaga tcctctgtga cgcctccgtg atgagcttta ccgccggatc ctactcttcg       960
tatgtgcaag tccggggatc cgtcccccctg tactggagcc aggacatctc cactatgatg      1020
cccaagcccc ctatcaccct ggaccaggcc gatcctttcg cacacgtggc tgccctgcac      1080
ttcgaccaga tgttccagcg gttcggctcc cctatcatca tcctgaactt ggtcaaggaa      1140
cgggagaagc ggaagcatga gaggattctg tccgaggagc tcgtggccgc ggtgacctac      1200
ctgaatcagt tcctcccgcc cgaacatacc atcgtgtata tcccctggga tatggccaag      1260
tacactaagt ccaagctgtg caatgtgctg gaccgcctta acgtcatcgc ggaatccgtg      1320
gtcaagaaaa ccggattctt cgtgaataga ccggattcat actgctccat tctccggccc      1380
gatgaaaagt ggaacgaact gggcggttgc gtcatcccga ctggccggct ccagaccggc      1440
atccttagga ccaactgcgt ggactgcctg gacagaacca acacggccca attcatggtc      1500
gggaaatgtg ccctggccta ccaactgtac tccctgggac tgatcgacaa gccgaacttg      1560
caattcgata ctgacgccgt gcggctgttc gaagaactgt acgaggatca cggcgacacc      1620
ctgagcctgc agtacggcgg aagccagctc gtgcatagag tgaaaaccta caggaagatt      1680
```

```
gctccgtgga ctcagcactc gaaggacatc atgcagaccc tcagccgcta ctactccaat    1740
gccttctccg acgccgaccg ccaggactcc attaacctct tcctgggagt gttccaccca    1800
accgagggaa agccccacct gtgggaactg cctactgatt tctacttgca tcacaagaac    1860
accatgagac tcctgcccac ccggcgctcc tacacttact ggtggacccc tgaagtgatc    1920
aagcacctcc cgctgccgta cgacgaggtc atctgcgccg tgaacctgaa aaagctgatc    1980
gtcaaaaagt tccataaata tgaagaagaa atcgacattc acaacgaatt cttccggcca    2040
tacgagctgt cctcgttcga cgacaccttt tgtctggcga tgacctcatc cgcccgcgat    2100
ttcatgccta agactgtggg gatcgacccc agccccttca ccgtccgcaa gcctgacgag    2160
actggaaagt cggtgctcgg caacaagagc aacaggaag aagcggtgct tcagagaaag    2220
actgctgcct cggcgccacc gccgccttcc gaagaagccg tgtcgtcatc ctcggaagat    2280
gacagcggaa ccgaccgcga ggaggagggg tccgtgagcc agcggtccac cccggtcaag    2340
atgactgacg ccggggactc ggccaaggtc accgaaaacg tggtgcaacc catgaaggaa    2400
ctgtacggca tcaaccttag cgacggcttg tctgaagagg acttctccat ctactctcgg    2460
tttgtgcagc tggggcagag ccagcacaag caggacaaga attcccaaca gccgtgcagc    2520
agatgctccg acggagtgat taagctgact ccgattagcg cgttctcgca agataacatc    2580
tacgaagtgc aaccccctcg cgtggacagg aagtccaccg agattttcca ggcccacatc    2640
caagcatccc agggaatcat gcagcccctc gggaaagagg actcctccat gtaccgggag    2700
tacatcagaa accgctacct g                                              2721

<210> SEQ ID NO 2
<211> LENGTH: 306
<212> TYPE: DNA
<213> ORGANISM: Artificial
<220> FEATURE:
<223> OTHER INFORMATION: Chicken beta-actin promoter

<400> SEQUENCE: 2
tacgtattag tcatcgctat taccatggtc gaggtgagcc ccacgttctg cttcactctc     60
cccatctccc cccctccc accccaatt ttgtatttat ttatttttta attattttgt       120
gcagcgatgg gggcggggggg gggggggggg cgcgcgccag gcggggcggg gcggggcgag   180 ggcggggcg gggcgaggcg gagaggtgcg gcggcagcca atcagagcgg cgcgctccga    240
aagtttcctt ttatggcgag gcggcggcgg cggcggccct ataaaaagcg aagcgcgcgg   300
cgggcg                                                              306

<210> SEQ ID NO 3
<211> LENGTH: 1068
<212> TYPE: DNA
<213> ORGANISM: Artificial
<220> FEATURE:
<223> OTHER INFORMATION: Chicken beta-actin exon 1 and intron

<400> SEQUENCE: 3
ggagtcgctg cgacgctgcc ttcgccccgt gccccgctcc gccgccgcct cgcgccgccc     60
gccccggctc tgactgaccg cgttactccc acaggtgagc gggcgggacg gcccttctcc    120
tccgggctgt aattagcgct tggtttaatg acggcttgtt tcttttctgt ggctgcgtga    180
aagccttgag gggctccggg agggccctt gtgcggggg gagcggctcg ggggtgcgt     240 gcgtgtgtgt gtgcgtgggg agcgccgcgt gcggcccgcg ctgcccggcg gctgtgagcg    300
```

| | |
|---|---|
| ctgcgggcgc ggcgcggggc tttgtgcgct ccgcagtgtg cgcgagggga gcgcggccgg | 360 |
| gggcggtgcc ccgcggtgcg ggggggggctg cgaggggaac aaaggctgcg tgcggggtgt | 420 |
| gtgcgtgggg gggtgagcag ggggtatggg cgcggcggtc gggctgtaac ccccccctgc | 480 |
| accccctcc ccgagttgct gagcacggcc cggcttcggg tgcggggctc cgtacggggc | 540 |
| gtggcgcggg gctcgccgtg ccgggcgggg ggtggcggca ggtgggggtg ccgggcgggg | 600 |
| cggggccgcc tcgggccggg gagggctcgg gggagggggcg cggcggcccc cggagcgccg | 660 |
| gcggctgtcg aggcgcggcg agccgcagcc attgcctttt atggtaatcg tgcgagaggg | 720 |
| cgcagggact tcctttgtcc caaatctgtg cggagccgaa atctgggagg cgccgccgca | 780 |
| cccctctag cgggcgcggg gcgaagcggt gcggcgccgg caggaaggaa atgggcgggg | 840 |
| agggccttcg tgcgtcgccg cgccgccgtc cccttctccc tctccagcct cggggctgtc | 900 |
| cgcggggggga cggctgcctt cggggggggac ggggcagggc ggggttcggc ttctggcgtg | 960 |
| tgaccggcgg ctctagagcc tctgctaacc atgttcatgc cttcttcttt ttcctacagc | 1020 |
| tcctgggcaa cgtgctggtt attgtgctgt ctcatcattt tggcaaag | 1068 |

<210> SEQ ID NO 4
<211> LENGTH: 239
<212> TYPE: DNA
<213> ORGANISM: Artificial
<220> FEATURE:
<223> OTHER INFORMATION: Cytomegalovirus enhancer

<400> SEQUENCE: 4

| | |
|---|---|
| tggcccgcct ggctgaccgc ccaacgaccc ccgcccattg acgtcaatag taacgccaat | 60 |
| agggactttc cattgacgtc aatgggtgga gtatttacgg taaactgccc acttggcagt | 120 |
| acatcaagtg tatcatatgc caagtacgcc ccctattgac gtcaatgacg gtaaatggcc | 180 |
| cgcctggcat tatgcccagt acatgacctt atgggacttt cctacttggc agtacatct | 239 |

<210> SEQ ID NO 5
<211> LENGTH: 48
<212> TYPE: DNA
<213> ORGANISM: Artificial
<220> FEATURE:
<223> OTHER INFORMATION: synthetic polyadenylation signal (SpA)

<400> SEQUENCE: 5

| | |
|---|---|
| aataaagagc tcagatgcat cgatcagagt gtgttggttt tttgtgtg | 48 |

<210> SEQ ID NO 6
<211> LENGTH: 4800
<212> TYPE: DNA
<213> ORGANISM: Artificial
<220> FEATURE:
<223> OTHER INFORMATION: FIG4 expression cassette

<400> SEQUENCE: 6

| | |
|---|---|
| gggggggggg gggggggttg gccactccct ctctgcgcgc tcgctcgctc actgaggccg | 60 |
| ggcgaccaaa ggtcgcccga cgcccgggct ttgcccgggc ggcctcagtg agcgagcgag | 120 |
| cgcgcagaga gggagtggcc aactccatca ctaggggttc ctagatctga attcggtacc | 180 |
| cgttacataa cttacggtaa atggcccgcc tggctgaccg cccaacgacc cccgcccatt | 240 |
| gacgtcaata gtaacgccaa tagggacttt ccattgacgt caatgggtgg agtatttacg | 300 |
| gtaaactgcc cacttggcag tacatcaagt gtatcatatg ccaagtacgc cccctattga | 360 |
| cgtcaatgac ggtaaatggc ccgcctggca ttatgcccag tacatgacct tatgggactt | 420 |

-continued

```
tcctacttgg cagtacatct acgtattagt catcgctatt accatggtcg aggtgagccc      480
cacgttctgc ttcactctcc ccatctcccc ccctcccca ccccaatttt tgtatttatt       540
tattttttaa ttattttgtg cagcgatggg ggcggggggg ggggggggc gcgcgccagg       600 cggggcgggg cggggcgagg ggcgggcgg ggcgaggcg aaaggtgcgg cggcagccaa        660
tcagagcggc gcgctccgaa agtttccttt tatggcgagg cggcggcggc ggcggcccta      720
taaaaagcga agcgcgcggc gggcgggagt cgctgcgacg ctgccttcgc cccgtgcccc      780
gctccgccgc cgcctcgcgc cgcccgcccc ggctctgact gaccgcgtta ctcccacagg      840
tgagcgggcg ggacgcccct tctcctccgg gctgtaatta gcgcttggtt taatgacggc      900 ttgtttctt tctgtggctg cgtgaaagcc ttgaggggct ccgggagggc cctttgtgcg       960
ggggggagcg gctcggggg tgcgtgcgtg tgtgtgtgcg tggggagcgc gcgtgcggc       1020 ccgcgctgcc cggcggctgt gagcgctgcg ggcgcggcgc ggggctttgt gcgctccgca     1080
gtgtgcgcga ggggagcgcg gccggggcg gtgcccgcg gtgcggggg ggctgcgagg       1140 ggaacaaagg ctgcgtgcgg ggtgtgtgcg tgggggggtg agcagggggt atgggcgcgg     1200
cggtcgggct gtaacccccc cctgcacccc cctccccgag ttgctgagca cggcccggct     1260
tcgggtgcgg ggctccgtac ggggcgtggc gcggggctcg ccgtgccggg cgggggtgg    1320 cggcaggtgg gggtgccggg cggggcgggg ccgcctcggg ccggggaggg ctcggggag      1380 gggcgcggcg gcccccggag cgccggcggc tgtcgaggcg cggcgagccg cagccattgc     1440
cttttatggt aatcgtgcga gagggcgcag ggacttcctt tgtcccaaat ctgtgcggag     1500
ccgaaatctg ggaggcgccg ccgcaccccc tctagcgggc gcggggcgaa gcggtgcggc     1560
gccggcagga aggaaatggg cggggagggc cttcgtgcgt cgccgcgccg ccgtcccctt     1620
ctccctctcc agcctcgggg ctgtccgcgg ggggacggct gccttcgggg gggacgggc     1680 agggcggggt tcggcttctg gcgtgtgacc ggcggctcta gagcctctgc taaccatgtt     1740
catgccttct tcttttttcct acagctcctg ggcaacgtgc tggttattgt gctgtctcat   1800
cattttggca aagaccggtt ccggacgcca ccatgccaac tgccgccgcc ccaatcattt     1860
catcagtgca aaagcttgtg ctctacgaga caagagctcg gtatttcctg gtcggctcca    1920
acaacgcaga aaccaagtac agagtgctta agattgaccg caccgaaccg aaggacctcg    1980
tgattattga cgatcgccac gtgtacactc agcaagaagt gcgcgaactc ttgggacgcc    2040
tggacctggg caaccgaacc aaaatgggcc agaagggctc ctccggtctg tttcgggcag    2100
tgtcggcttt cggcgtcgtg ggattcgtgc gattccttga ggggtactat attgtgctga    2160
tcacgaagcg gcgcaagatg gccgacatcg gaggacacgc tatatacaag gtcgaggaca    2220
ccaacatgat ctacattccg aacgattcag tcagagtgac ccaccccgat gaagcccgct    2280
accttagaat cttccagaac gtggatctct cctcgaactt ttacttctca tactcgtacg    2340
acctgtccca ctcgctgcag tacaacctga ccgtgctgcg gatgcctctg gagatgctca    2400
agtccgagat gactcaaaat cggcaggaat ccttcgacat cttcgaggac gagggtctga    2460
tcactcaagg agggtcggga gtgttcggca tttgcagcga accctacatg aaatacgtgt    2520
ggaacgagag gctcctggac attatcaaga gcactgtgca ccgggactgg ctgctgtaca    2580
tcatccatgg attctgtgga cagtcaaagc tcctgatcta tggccggcct gtgtacgtga    2640
ctctgatcgc ccgccgctcc tcgaagttcg cgggtacccg gtttctcaag cgcggtgcta    2700
actgcgaggg ggatgtggcc aacgaagtgg aaaccgagca gatcctctgt gacgcctccg    2760
```

```
tgatgagctt taccgccgga tcctactctt cgtatgtgca agtccgggga tccgtccccc    2820
tgtactggag ccaggacatc tccactatga tgcccaagcc ccctatcacc ctggaccagg    2880
ccgatccttt cgcacacgtg gctgccctgc acttcgacca gatgttccag cggttcggct    2940
cccctatcat catcctgaac ttggtcaagg aacgggagaa gcggaagcat gagaggattc    3000
tgtccgagga gctcgtggcc gcggtgacct acctgaatca gttcctcccg cccgaacata    3060
ccatcgtgta tatccctggg gatatggcca agtacactaa gtccaagctg tgcaatgtgc    3120
tggaccgcct taacgtcatc gcggaatccg tggtcaagaa aaccggattc ttcgtgaata    3180
gaccggattc atactgctcc attctccggc ccgatgaaaa gtggaacgaa ctgggcggtt    3240
gcgtcatccc gactggccgg ctccagaccg gcatccttag gaccaactgc gtggactgcc    3300
tggacagaac caacacggcc caattcatgg tcgggaaatg tgccctggcc taccaactgt    3360
actccctggg actgatcgac aagccgaact tgcaattcga tactgacgcc gtgcggctgt    3420
tcgaagaact gtacgaggat cacggcgaca ccctgagcct gcagtacggc ggaagccagc    3480
tcgtgcatag agtgaaaacc tacaggaaga ttgctccgtg gactcagcac tcgaaggaca    3540
tcatgcagac cctcagccgc tactactcca atgccttctc cgacgccgac cgccaggact    3600
ccattaacct cttcctggga gtgttccacc caaccgaggg aaagccccac ctgtgggaac    3660
tgcctactga tttctacttg catcacaaga acaccatgag actcctgccc acccggcgct    3720
cctacactta ctggtggacc cctgaagtga tcaagcacct cccgctgccg tacgacgagg    3780
tcatctgcgc cgtgaacctg aaaaagctga tcgtcaaaaa gttccataaa tatgaagaag    3840
aaatcgacat tcacaacgaa ttcttccggc catacgagct gtcctcgttc gacgacacct    3900
tttgtctggc gatgacctca tccgcccgcg atttcatgcc taagactgtg gggatcgacc    3960
ccagcccctt caccgtccgc aagcctgacg agactggaaa gtcggtgctc ggcaacaaga    4020
gcaacaggga agaagcggtg cttcagagaa agactgctgc ctcggcgcca ccgccgcctt    4080
ccgaagaagc cgtgtcgtca tcctcggaag atgacagcgg aaccgaccgc gaggaggagg    4140
ggtccgtgag ccagcggtcc accccggtca agatgactga cgccggggac tcggccaagg    4200
tcaccgaaaa cgtggtgcaa cccatgaagg aactgtacgg catcaacctt agcgacggct    4260
tgtctgaaga ggacttctcc atctactctc ggtttgtgca gctggggcag agccagcaca    4320
agcaggacaa gaattcccaa cagccgtgca gcagatgctc cgacggagtg attaagctga    4380
ctccgattag cgcgttctcg caagataaca tctacgaagt gcaacccct cgcgtggaca    4440
ggaagtccac cgagattttc caggcccaca tccaagcatc ccagggaatc atgcagcccc    4500
tcgggaaaga ggactcctcc atgtaccggg agtacatcag aaaccgctac ctgtagtaac    4560
tcgagaataa agagctcaga tgcatcgatc agagtgtgtt ggttttttgt gtgacgcgtg    4620
catgctgggg agagatctag gaacccctag tgatggagtt ggccactccc tctctgcgcg    4680
ctcgctcgct cactgaggcc gcccgggcaa agcccgggcg tcgggcgacc tttggtcgcc    4740
cggcctcagt gagcgagcga gcgcgcagag agggagtggc caaccccccc cccccccccc    4800
```

<210> SEQ ID NO 7
<211> LENGTH: 907
<212> TYPE: PRT
<213> ORGANISM: Artificial Sequence
<220> FEATURE:
<223> OTHER INFORMATION: Optimized hFIG4

<400> SEQUENCE: 7

Met Pro Thr Ala Ala Ala Pro Ile Ile Ser Ser Val Gln Lys Leu Val

```
 1               5                  10                 15
Leu Tyr Glu Thr Arg Ala Arg Tyr Phe Leu Val Gly Ser Asn Asn Ala
                20                 25                 30
Glu Thr Lys Tyr Arg Val Leu Lys Ile Asp Arg Thr Glu Pro Lys Asp
                35                 40                 45
Leu Val Ile Ile Asp Asp Arg His Val Tyr Thr Gln Gln Glu Val Arg
                50                 55                 60
Glu Leu Leu Gly Arg Leu Asp Leu Gly Asn Arg Thr Lys Met Gly Gln
 65                 70                 75                 80
Lys Gly Ser Ser Gly Leu Phe Arg Ala Val Ser Ala Phe Gly Val Val
                85                 90                 95
Gly Phe Val Arg Phe Leu Glu Gly Tyr Tyr Ile Val Leu Ile Thr Lys
               100                105                110
Arg Arg Lys Met Ala Asp Ile Gly Gly His Ala Ile Tyr Lys Val Glu
               115                120                125
Asp Thr Asn Met Ile Tyr Ile Pro Asn Asp Ser Val Arg Val Thr His
               130                135                140
Pro Asp Glu Ala Arg Tyr Leu Arg Ile Phe Gln Asn Val Asp Leu Ser
145                150                155                160
Ser Asn Phe Tyr Phe Ser Tyr Ser Tyr Asp Leu Ser His Ser Leu Gln
               165                170                175
Tyr Asn Leu Thr Val Leu Arg Met Pro Leu Glu Met Leu Lys Ser Glu
               180                185                190
Met Thr Gln Asn Arg Gln Glu Ser Phe Asp Ile Phe Glu Asp Glu Gly
               195                200                205
Leu Ile Thr Gln Gly Gly Ser Gly Val Phe Gly Ile Cys Ser Glu Pro
210                215                220
Tyr Met Lys Tyr Val Trp Asn Gly Glu Leu Leu Asp Ile Ile Lys Ser
225                230                235                240
Thr Val His Arg Asp Trp Leu Leu Tyr Ile Ile His Gly Phe Cys Gly
               245                250                255
Gln Ser Lys Leu Leu Ile Tyr Gly Arg Pro Val Tyr Val Thr Leu Ile
               260                265                270
Ala Arg Arg Ser Ser Lys Phe Ala Gly Thr Arg Phe Leu Lys Arg Gly
               275                280                285
Ala Asn Cys Glu Gly Asp Val Ala Asn Glu Val Glu Thr Glu Gln Ile
               290                295                300
Leu Cys Asp Ala Ser Val Met Ser Phe Thr Ala Gly Ser Tyr Ser Ser
305                310                315                320
Tyr Val Gln Val Arg Gly Ser Val Pro Leu Tyr Trp Ser Gln Asp Ile
               325                330                335
Ser Thr Met Met Pro Lys Pro Pro Ile Thr Leu Asp Gln Ala Asp Pro
               340                345                350
Phe Ala His Val Ala Ala Leu His Phe Asp Gln Met Phe Gln Arg Phe
               355                360                365
Gly Ser Pro Ile Ile Ile Leu Asn Leu Val Lys Glu Arg Glu Lys Arg
               370                375                380
Lys His Glu Arg Ile Leu Ser Glu Glu Leu Val Ala Ala Val Thr Tyr
385                390                395                400
Leu Asn Gln Phe Leu Pro Pro Glu His Thr Ile Val Tyr Ile Pro Trp
               405                410                415
Asp Met Ala Lys Tyr Thr Lys Ser Lys Leu Cys Asn Val Leu Asp Arg
               420                425                430
```

```
Leu Asn Val Ile Ala Glu Ser Val Lys Lys Thr Gly Phe Phe Val
            435                 440                 445
Asn Arg Pro Asp Ser Tyr Cys Ser Ile Leu Arg Pro Asp Glu Lys Trp
450                 455                 460
Asn Glu Leu Gly Gly Cys Val Ile Pro Thr Gly Arg Leu Gln Thr Gly
465                 470                 475                 480
Ile Leu Arg Thr Asn Cys Val Asp Cys Leu Asp Arg Thr Asn Thr Ala
                485                 490                 495
Gln Phe Met Val Gly Lys Cys Ala Leu Ala Tyr Gln Leu Tyr Ser Leu
                500                 505                 510
Gly Leu Ile Asp Lys Pro Asn Leu Gln Phe Asp Thr Asp Ala Val Arg
            515                 520                 525
Leu Phe Glu Glu Leu Tyr Glu Asp His Gly Asp Thr Leu Ser Leu Gln
        530                 535                 540
Tyr Gly Gly Ser Gln Leu Val His Arg Val Lys Thr Tyr Arg Lys Ile
545                 550                 555                 560
Ala Pro Trp Thr Gln His Ser Lys Asp Ile Met Gln Thr Leu Ser Arg
                565                 570                 575
Tyr Tyr Ser Asn Ala Phe Ser Asp Ala Asp Arg Gln Asp Ser Ile Asn
            580                 585                 590
Leu Phe Leu Gly Val Phe His Pro Thr Glu Gly Lys Pro His Leu Trp
        595                 600                 605
Glu Leu Pro Thr Asp Phe Tyr Leu His His Lys Asn Thr Met Arg Leu
    610                 615                 620
Leu Pro Thr Arg Arg Ser Tyr Thr Tyr Trp Trp Thr Pro Glu Val Ile
625                 630                 635                 640
Lys His Leu Pro Leu Pro Tyr Asp Glu Val Ile Cys Ala Val Asn Leu
                645                 650                 655
Lys Lys Leu Ile Val Lys Lys Phe His Lys Tyr Glu Glu Ile Asp
            660                 665                 670
Ile His Asn Glu Phe Phe Arg Pro Tyr Glu Leu Ser Ser Phe Asp Asp
        675                 680                 685
Thr Phe Cys Leu Ala Met Thr Ser Ser Ala Arg Asp Phe Met Pro Lys
    690                 695                 700
Thr Val Gly Ile Asp Pro Ser Pro Phe Thr Val Arg Lys Pro Asp Glu
705                 710                 715                 720
Thr Gly Lys Ser Val Leu Gly Asn Lys Ser Asn Arg Glu Glu Ala Val
                725                 730                 735
Leu Gln Arg Lys Thr Ala Ala Ser Ala Pro Pro Pro Ser Glu Glu
            740                 745                 750
Ala Val Ser Ser Ser Glu Asp Asp Ser Gly Thr Asp Arg Glu Glu
        755                 760                 765
Glu Gly Ser Val Ser Gln Arg Ser Thr Pro Val Lys Met Thr Asp Ala
770                 775                 780
Gly Asp Ser Ala Lys Val Thr Glu Asn Val Val Gln Pro Met Lys Glu
785                 790                 795                 800
Leu Tyr Gly Ile Asn Leu Ser Asp Gly Leu Ser Glu Glu Asp Phe Ser
                805                 810                 815
Ile Tyr Ser Arg Phe Val Gln Leu Gly Gln Ser Gln His Lys Gln Asp
            820                 825                 830
Lys Asn Ser Gln Gln Pro Cys Ser Arg Cys Ser Asp Gly Val Ile Lys
        835                 840                 845
```

Leu Thr Pro Ile Ser Ala Phe Ser Gln Asp Asn Ile Tyr Glu Val Gln
850                 855                 860

Pro Pro Arg Val Asp Arg Lys Ser Thr Glu Ile Phe Gln Ala His Ile
865                 870                 875                 880

Gln Ala Ser Gln Gly Ile Met Gln Pro Leu Gly Lys Glu Asp Ser Ser
                885                 890                 895

Met Tyr Arg Glu Tyr Ile Arg Asn Arg Tyr Leu
            900                 905

<210> SEQ ID NO 8
<211> LENGTH: 907
<212> TYPE: PRT
<213> ORGANISM: Macaca mulatta

<400> SEQUENCE: 8

Met Pro Ser Ala Ala Pro Ile Ile Ser Ser Val Gln Lys Leu Val
1               5                   10                  15

Leu Tyr Glu Thr Arg Ala Arg Tyr Phe Leu Val Gly Ser Asn Asn Ala
            20                  25                  30

Glu Thr Lys Tyr Arg Val Leu Lys Ile Asp Arg Thr Glu Pro Lys Asp
        35                  40                  45

Leu Val Ile Ile Asp Asp Arg His Val Tyr Thr Gln Gln Glu Val Arg
50                  55                  60

Glu Leu Leu Gly Arg Leu Asp Leu Gly Asn Arg Thr Lys Met Gly Gln
65                  70                  75                  80

Lys Gly Ser Ser Gly Leu Phe Arg Ala Val Ser Ala Phe Gly Val Val
                85                  90                  95

Gly Phe Val Arg Phe Leu Glu Gly Tyr Tyr Ile Val Leu Ile Thr Lys
            100                 105                 110

Arg Arg Lys Met Ala Asp Ile Gly Gly His Ala Ile Tyr Lys Val Glu
        115                 120                 125

Asp Thr Asn Met Ile Tyr Ile Pro Asn Asp Ser Val Arg Val Thr His
130                 135                 140

Pro Asp Glu Ala Arg Tyr Leu Arg Ile Phe Gln Asn Val Asp Leu Ser
145                 150                 155                 160

Ser Asn Phe Tyr Phe Ser Tyr Ser Tyr Asp Leu Ser His Ser Leu Gln
                165                 170                 175

Tyr Asn Leu Thr Val Leu Arg Met Pro Leu Glu Met Leu Lys Ser Glu
            180                 185                 190

Thr Thr Gln Asn Arg Gln Glu Ser Phe Asp Ile Phe Glu Asp Glu Gly
        195                 200                 205

Leu Ile Thr Gln Gly Gly Ser Gly Val Phe Gly Ile Cys Ser Glu Pro
210                 215                 220

Tyr Met Lys Tyr Val Trp Asn Gly Glu Leu Leu Asp Ile Ile Lys Asn
225                 230                 235                 240

Thr Val His Arg Asp Trp Leu Leu Tyr Ile His Gly Phe Cys Gly
                245                 250                 255

Gln Ser Lys Leu Leu Ile Tyr Gly Arg Pro Val Tyr Val Thr Leu Ile
            260                 265                 270

Ala Arg Arg Ser Ser Lys Phe Ala Gly Thr Arg Phe Leu Lys Arg Gly
        275                 280                 285

Ala Asn Cys Glu Gly Asp Val Ala Asn Glu Val Glu Thr Glu Gln Ile
290                 295                 300

Leu Cys Asp Ala Ser Val Met Ser Phe Thr Ala Gly Ser Tyr Ser Ser
305                 310                 315                 320

```
Tyr Val Gln Val Arg Gly Ser Val Pro Leu Tyr Trp Ser Gln Asp Ile
                325                 330                 335

Ser Thr Met Met Pro Lys Pro Pro Ile Thr Leu Asp Gln Ala Asp Pro
            340                 345                 350

Phe Ala His Val Ala Ala Leu His Phe Asp Gln Met Phe Gln Arg Phe
        355                 360                 365

Gly Ser Pro Ile Ile Ile Leu Asn Leu Val Lys Glu Arg Glu Lys Arg
    370                 375                 380

Lys His Glu Arg Ile Leu Ser Glu Glu Leu Val Ala Ala Val Thr Tyr
385                 390                 395                 400

Leu Asn Gln Phe Leu Pro Pro Glu His Thr Ile Val Tyr Ile Pro Trp
                405                 410                 415

Asp Met Ala Lys Tyr Thr Lys Ser Lys Leu Cys Asn Val Leu Asp Arg
            420                 425                 430

Leu Asn Val Ile Ala Glu Ser Val Val Lys Lys Thr Gly Phe Phe Val
        435                 440                 445

Asn Arg Pro Asp Ser Tyr Cys Ser Ile Leu Arg Pro Asp Glu Lys Trp
    450                 455                 460

Asn Glu Leu Gly Gly Cys Val Ile Pro Thr Gly Arg Leu Gln Thr Gly
465                 470                 475                 480

Ile Leu Arg Thr Asn Cys Val Asp Cys Leu Asp Arg Thr Asn Thr Ala
                485                 490                 495

Gln Phe Met Val Gly Lys Cys Ala Leu Ala Tyr Gln Leu Tyr Ser Leu
            500                 505                 510

Gly Leu Ile Asp Lys Pro Asn Leu Gln Phe Asp Thr Asp Ala Val Arg
        515                 520                 525

Leu Phe Glu Glu Leu Tyr Glu Asp His Gly Asp Thr Leu Ser Leu Gln
    530                 535                 540

Tyr Gly Gly Ser Gln Leu Val His Arg Val Lys Thr Tyr Arg Lys Ile
545                 550                 555                 560

Ala Pro Trp Thr Gln His Ser Lys Asp Ile Met Gln Thr Leu Ser Arg
                565                 570                 575

Tyr Tyr Ser Asn Ala Phe Ser Asp Ala Asp Arg Gln Asp Ser Ile Asn
            580                 585                 590

Leu Phe Leu Gly Val Phe His Pro Thr Glu Gly Lys Pro His Leu Trp
        595                 600                 605

Glu Leu Pro Thr Asp Phe Tyr Leu His His Lys Asn Thr Met Arg Leu
    610                 615                 620

Leu Pro Thr Arg Arg Ser Tyr Thr Tyr Trp Trp Thr Pro Glu Val Ile
625                 630                 635                 640

Lys His Leu Pro Leu Pro Tyr Asp Glu Val Ile Cys Ala Val Asn Leu
                645                 650                 655

Lys Lys Leu Ile Val Lys Lys Phe His Lys Tyr Glu Glu Ile Asp
            660                 665                 670

Ile His Asn Glu Phe Phe Arg Pro Tyr Glu Leu Ser Ser Phe Asp Asp
        675                 680                 685

Thr Phe Cys Leu Ala Met Thr Ser Ser Ala Arg Asp Phe Met Pro Lys
    690                 695                 700

Thr Val Gly Ile Asp Pro Ser Pro Phe Thr Val Arg Lys Pro Asp Glu
705                 710                 715                 720

Thr Gly Lys Ser Val Leu Gly Asn Lys Ser Asn Arg Glu Glu Ala Val
                725                 730                 735
```

-continued

```
Leu Gln Arg Lys Thr Ala Ala Ser Ala Pro Pro Pro Ser Glu Glu
                740                 745                 750

Ala Val Ser Ser Ser Glu Asp Asp Ser Gly Thr Asp Arg Glu Glu
        755                 760                 765

Glu Gly Ser Val Ser Gln Arg Ser Thr Pro Val Lys Met Thr Asp Ala
    770                 775                 780

Gly Asp Ser Ala Lys Val Thr Glu Asn Val Val Gln Pro Met Lys Glu
785                 790                 795                 800

Leu Tyr Gly Ile Asn Leu Ser Asp Gly Leu Ser Glu Glu Asp Phe Ser
                805                 810                 815

Ile Tyr Ser Arg Phe Val Gln Leu Gly Gln Ser Gln His Lys Gln Asp
            820                 825                 830

Lys Asn Ser Gln Gln Pro Cys Ser Arg Cys Ser Asp Gly Val Ile Lys
        835                 840                 845

Leu Thr Pro Ile Ser Ala Phe Ser Gln Asp Asn Ile Tyr Glu Val Gln
    850                 855                 860

Pro Pro Arg Val Asp Arg Lys Ser Thr Glu Ile Phe Gln Ala His Ile
865                 870                 875                 880

Gln Ala Ser Gln Gly Ile Met Gln Pro Leu Gly Lys Glu Asp Ser Ala
                885                 890                 895

Met Tyr Arg Glu Tyr Ile Arg Asn Arg Tyr Leu
            900                 905

<210> SEQ ID NO 9
<211> LENGTH: 907
<212> TYPE: PRT
<213> ORGANISM: Mus musculus

<400> SEQUENCE: 9

Met Pro Thr Ala Ala Pro Ile Ile Ser Ser Val Gln Lys Leu Val
1               5                   10                  15

Leu Tyr Glu Thr Arg Ala Arg Tyr Phe Leu Val Gly Ser Asn His Ala
            20                  25                  30

Glu Thr Lys Tyr Arg Val Leu Lys Ile Asp Arg Thr Glu Pro Lys Asp
        35                  40                  45

Leu Val Val Ile Asp Asp Arg His Val Tyr Thr Gln Gln Glu Val Arg
    50                  55                  60

Glu Leu Leu Gly Arg Leu Asp Leu Gly Asn Arg Thr Lys Met Ser Gln
65                  70                  75                  80

Lys Gly Ser Ser Gly Leu Phe Arg Ala Val Ser Ala Phe Gly Val Val
                85                  90                  95

Gly Phe Val Arg Phe Leu Glu Gly Tyr Tyr Ile Val Leu Ile Thr Lys
            100                 105                 110

Arg Arg Lys Met Ala Asp Ile Gly Gly His Ala Ile Tyr Lys Ile Glu
        115                 120                 125

Asp Thr Ser Met Ile Tyr Ile Pro Asn Asp Ser Val Arg Ile Ser His
    130                 135                 140

Pro Asp Glu Ala Arg Tyr Leu Arg Ile Phe Gln Asn Val Asp Leu Ser
145                 150                 155                 160

Ser Asn Phe Tyr Phe Ser Tyr Ser Tyr Asp Leu Ser His Ser Leu Gln
                165                 170                 175

Tyr Asn Leu Thr Val Leu Arg Met Pro Leu Glu Met Leu Lys Ser Glu
            180                 185                 190

Thr Ser Lys Ala Cys Gln Glu Ser Phe Asp Ile Phe Glu Asp Glu Gly
        195                 200                 205
```

```
Leu Ile Thr Gln Gly Gly Ser Gly Val Phe Gly Ile Ser Glu Pro
    210                 215                 220
Tyr Met Lys Tyr Val Trp Asn Gly Glu Leu Leu Asp Ile Ile Lys Asn
225                 230                 235                 240
Thr Val His Arg Asp Trp Leu Leu Tyr Ile Ile His Gly Phe Cys Gly
                245                 250                 255
Gln Ser Lys Leu Leu Ile Tyr Gly Arg Pro Val Tyr Val Thr Leu Ile
                260                 265                 270
Ala Arg Arg Ser Ser Arg Phe Ala Gly Thr Arg Phe Leu Lys Arg Gly
            275                 280                 285
Ala Asn Cys Glu Gly Asp Val Ala Asn Glu Val Glu Thr Glu Gln Ile
        290                 295                 300
Leu Cys Asp Ala Ser Val Met Ser Phe Thr Ala Gly Ser Tyr Ser Ser
305                 310                 315                 320
Tyr Val Gln Val Arg Gly Ser Val Pro Leu Phe Trp Ser Gln Asp Ile
                325                 330                 335
Ser Thr Met Met Pro Lys Pro Pro Ile Thr Leu Asp Gln Ala Asp Pro
                340                 345                 350
Phe Ala His Val Ala Ala Leu His Phe Asp Gln Met Leu Gln Arg Phe
                355                 360                 365
Gly Ser Pro Ile Ile Ile Leu Asn Leu Val Lys Glu Arg Glu Lys Arg
370                 375                 380
Lys His Glu Arg Ile Leu Ser Glu Glu Leu Val Ala Ala Val Thr Tyr
385                 390                 395                 400
Leu Asn Gln Phe Leu Pro Pro Glu His Thr Ile Val Tyr Ile Pro Trp
                405                 410                 415
Asp Met Ala Lys Tyr Thr Lys Ser Lys Leu Cys Asn Val Leu Asp Arg
                420                 425                 430
Leu Asn Val Ile Ala Glu Ser Val Val Lys Lys Thr Gly Phe Phe Val
            435                 440                 445
Asn Arg Pro Asp Ser Tyr Cys Ser Ile Leu Arg Pro Asp Glu Lys Trp
        450                 455                 460
Asn Glu Leu Gly Gly His Val Ile Pro Thr Gly Arg Leu Gln Thr Gly
465                 470                 475                 480
Ile Leu Arg Thr Asn Cys Val Asp Cys Leu Asp Arg Thr Asn Thr Ala
                485                 490                 495
Gln Phe Met Val Gly Lys Cys Ala Leu Ala Tyr Gln Leu Tyr Ser Leu
                500                 505                 510
Gly Leu Ile Asp Lys Pro Asn Leu Gln Phe Asp Thr Asp Ala Val Arg
            515                 520                 525
Leu Phe Glu Glu Leu Tyr Glu Asp His Gly Asp Thr Leu Ser Leu Gln
        530                 535                 540
Tyr Gly Gly Ser Gln Leu Val His Arg Val Lys Thr Tyr Arg Lys Ile
545                 550                 555                 560
Ala Pro Trp Thr Gln His Ser Lys Asp Ile Met Gln Thr Leu Ser Arg
                565                 570                 575
Tyr Tyr Ser Asn Ala Phe Ser Asp Ala Asp Arg Gln Asp Ser Ile Asn
                580                 585                 590
Leu Phe Leu Gly Val Phe His Pro Thr Glu Gly Lys Pro His Leu Trp
            595                 600                 605
Glu Leu Pro Thr Asp Phe Tyr Leu His His Lys Asn Thr Met Ser Leu
        610                 615                 620
```

```
Leu Pro Pro Arg Arg Ser Tyr Thr Tyr Trp Trp Thr Pro Glu Val Val
625                 630                 635                 640

Lys His Leu Pro Leu Pro Tyr Asp Glu Val Ile Cys Ala Ala Asn Leu
            645                 650                 655

Lys Lys Leu Met Val Lys Lys Phe His Arg Trp Glu Glu Ile Asp
            660                 665                 670

Ile His Asn Glu Phe Phe Arg Pro Tyr Glu Leu Ser Ser Phe Asp Asp
            675                 680                 685

Thr Phe Cys Leu Ala Met Thr Ser Ser Ala Arg Asp Phe Met Pro Lys
    690                 695                 700

Thr Val Gly Ile Asp Pro Ser Pro Phe Thr Val Arg Lys Pro Asp Glu
705                 710                 715                 720

Thr Gly Lys Ser Val Leu Gly Asn Lys Asn Thr Arg Glu Glu Ala Val
                725                 730                 735

Leu Gln Arg Lys Thr Ala Ala Ser Ala Pro Pro Pro Ser Glu Glu
            740                 745                 750

Ala Val Ser Ser Ser Glu Asp Ser Gly Thr Asp Arg Glu Asp
        755                 760                 765

Glu Gly Ser Ile Ser Gln Arg Ser Thr Pro Val Lys Met Thr Asp Thr
770                 775                 780

Gly Asp Ser Ala Lys Ala Thr Glu Asn Val Val Gln Pro Met Lys Glu
785                 790                 795                 800

Val Tyr Gly Val Ser Leu Ser Ser Ser Leu Ser Glu Glu Asp His Ser
                805                 810                 815

Ile Tyr Ala Arg Phe Val Gln Leu Gly Gln Ser Gln His Lys Gln Asp
            820                 825                 830

Arg Gly Asn Gln Gln Leu Cys Ser Arg Cys Ser Asp Gly Val Ile Lys
            835                 840                 845

Leu Thr Pro Ile Ser Ala Phe Ser Gln Asp Asn Ile Tyr Glu Val Gln
    850                 855                 860

Pro Pro Arg Val Asp Arg Lys Ser Thr Glu Ile Phe Gln Ala His Ile
865                 870                 875                 880

Gln Ala Ser Gln Gly Ile Met Gln Pro Leu Gly Lys Glu Asp Thr Ala
                885                 890                 895

Met Tyr Arg Glu Tyr Ile Arg Asn Arg Tyr Leu
            900                 905

<210> SEQ ID NO 10
<211> LENGTH: 907
<212> TYPE: PRT
<213> ORGANISM: Rattus norvegicus

<400> SEQUENCE: 10

Met Pro Thr Ala Ala Pro Ile Ile Ser Ser Val Gln Lys Leu Val
1               5                   10                  15

Leu Tyr Glu Thr Arg Ala Arg Tyr Phe Leu Val Gly Ser Asn His Ala
            20                  25                  30

Glu Thr Lys Phe Arg Val Leu Lys Ile Asp Arg Thr Glu Pro Lys Asp
        35                  40                  45

Leu Val Val Ile Asp Asp Arg His Val Tyr Thr Gln Gln Glu Val Arg
    50                  55                  60

Glu Leu Leu Gly Arg Leu Asp Leu Gly Asn Arg Thr Lys Leu Ser Gln
65                  70                  75                  80

Lys Gly Ser Ser Gly Leu Phe Arg Ala Val Ser Ala Phe Gly Val Val
                85                  90                  95
```

```
Gly Phe Val Arg Phe Leu Glu Gly Tyr Tyr Ile Val Leu Ile Thr Lys
                100                 105                 110

Arg Arg Lys Met Ala Asp Ile Gly His Ala Ile Tyr Lys Ile Glu
            115                 120                 125

Asp Thr Ser Met Ile Tyr Ile Pro Asn Asp Ser Val Arg Ile Thr His
            130                 135                 140

Pro Asp Glu Ala Arg Tyr Leu Arg Ile Phe Gln Asn Val Asp Leu Ser
145                 150                 155                 160

Ser Asn Phe Tyr Phe Ser Tyr Ser Tyr Asp Leu Ser His Ser Leu Gln
                165                 170                 175

Tyr Asn Leu Thr Val Leu Arg Met Pro Leu Glu Met Leu Lys Ser Glu
            180                 185                 190

Thr Ser Lys Thr Cys Gln Glu Ser Phe Asp Ile Phe Glu Asp Glu Gly
            195                 200                 205

Leu Thr Thr Gln Gly Gly Ser Gly Val Phe Gly Ile Ser Ser Glu Pro
            210                 215                 220

Tyr Met Lys Tyr Val Trp Asn Gly Glu Leu Leu Asp Ile Ile Lys Asn
225                 230                 235                 240

Ser Val His Arg Asp Trp Leu Leu Tyr Ile Ile His Gly Phe Cys Gly
                245                 250                 255

Gln Ser Lys Leu Leu Ile Tyr Gly Arg Pro Val Tyr Val Thr Leu Ile
            260                 265                 270

Ala Arg Arg Ser Ser Arg Phe Ala Gly Thr Arg Phe Leu Lys Arg Gly
            275                 280                 285

Ala Asn Cys Glu Gly Asp Val Ala Asn Glu Val Thr Glu Gln Ile
            290                 295                 300

Leu Cys Asp Ala Ser Val Met Ser Phe Thr Ala Gly Ser Tyr Ser Ser
305                 310                 315                 320

Tyr Val Gln Val Arg Gly Ser Val Pro Leu Phe Trp Ser Gln Asp Ile
                325                 330                 335

Ser Thr Met Met Pro Lys Pro Pro Ile Thr Leu Asp Gln Ala Asp Pro
            340                 345                 350

Phe Ala His Ile Ala Ala Leu His Phe Asp Gln Met Leu Gln Arg Phe
            355                 360                 365

Gly Ser Pro Ile Ile Ile Leu Asn Leu Val Lys Glu Arg Glu Lys Arg
            370                 375                 380

Lys His Glu Arg Ile Leu Ser Glu Glu Leu Val Ala Ala Val Thr Tyr
385                 390                 395                 400

Leu Asn Gln Phe Leu Pro Pro Glu His Ser Ile Val Tyr Ile Pro Trp
                405                 410                 415

Asp Met Ala Lys Tyr Thr Lys Ser Lys Leu Cys Asn Val Leu Asp Arg
            420                 425                 430

Leu Asn Val Ile Ala Glu Ser Val Val Lys Lys Thr Gly Phe Phe Val
            435                 440                 445

Asn Arg Pro Asp Ser Tyr Cys Ser Val Leu Arg Pro Asp Glu Lys Trp
450                 455                 460

Asn Glu Leu Gly Gly Arg Val Ile Pro Thr Gly Arg Leu Gln Thr Gly
                470                 475                 480
465

Ile Leu Arg Thr Asn Cys Val Asp Cys Leu Asp Arg Thr Asn Thr Ala
            485                 490                 495

Gln Phe Met Val Gly Lys Cys Ala Leu Ala Tyr Gln Leu Tyr Ser Leu
            500                 505                 510
```

```
Gly Leu Ile Asp Lys Pro Asn Leu Gln Phe Asp Thr Asp Ala Val Arg
            515                 520                 525

Leu Phe Glu Glu Leu Tyr Glu Asp His Gly Asp Thr Leu Ser Leu Gln
530                 535                 540

Tyr Gly Gly Ser Gln Leu Val His Arg Val Lys Thr Tyr Arg Lys Ile
545                 550                 555                 560

Ala Pro Trp Thr Gln His Ser Lys Asp Ile Met Gln Thr Leu Ser Arg
                565                 570                 575

Tyr Tyr Ser Asn Ala Phe Ser Asp Ala Asp Arg Gln Asp Ser Ile Asn
            580                 585                 590

Leu Phe Leu Gly Val Phe His Pro Thr Glu Gly Lys Pro His Leu Trp
        595                 600                 605

Glu Leu Pro Thr Asp Phe Tyr Leu His His Lys Asn Thr Met Ser Leu
            610                 615                 620

Leu Pro Pro Lys Arg Ser Tyr Thr His Trp Trp Thr Pro Glu Val Val
625                 630                 635                 640

Lys His Leu Pro Leu Pro Tyr Asp Glu Val Ile Cys Ala Ala Asn Leu
                645                 650                 655

Lys Lys Leu Thr Val Lys Lys Phe His Arg Trp Glu Glu Ile Asp
            660                 665                 670

Ile His Asn Glu Phe Phe Arg Pro Tyr Glu Leu Ser Ser Phe Asp Asp
        675                 680                 685

Thr Phe Cys Leu Ala Met Thr Ser Ser Ala Arg Asp Phe Met Pro Lys
            690                 695                 700

Thr Ile Gly Ile Asp Pro Ser Pro Phe Thr Val Arg Lys Pro Asp Glu
705                 710                 715                 720

Thr Gly Lys Ser Val Leu Gly Asn Lys Ser Asn Arg Glu Glu Ala Val
                725                 730                 735

Leu Gln Arg Lys Thr Ala Ala Ser Ala Pro Pro Pro Ser Glu Glu
            740                 745                 750

Ala Val Ser Ser Ser Ser Glu Asp Asp Ser Gly Thr Asp Arg Glu Asp
        755                 760                 765

Glu Gly Ser Ile Ser Gln Arg Ser Thr Pro Val Lys Met Thr Asp Thr
770                 775                 780

Gly Asp Ser Ala Lys Val Thr Glu Ser Val Ala Gln Pro Met Lys Glu
785                 790                 795                 800

Val Tyr Gly Val Ser Leu Ser Arg Ser Leu Ser Glu Glu Asp His Ser
                805                 810                 815

Ile Tyr Ala Arg Phe Val Gln Leu Gly Gln Ser Gln His Arg Gln Asp
            820                 825                 830

Trp Ser Pro Gln Met Cys Ala Arg Cys Ser Asp Gly Val Ile Lys
        835                 840                 845

Leu Thr Pro Ile Ser Ala Phe Ser Gln Asp Asn Ile Tyr Glu Val Gln
            850                 855                 860

Pro Pro Arg Val Asp Arg Lys Ser Thr Glu Ile Phe Gln Ala His Ile
865                 870                 875                 880

Gln Ala Ser Gln Gly Ile Met Gln Pro Leu Gly Lys Glu Asp Thr Ala
                885                 890                 895

Ile Tyr Arg Glu Tyr Ile Arg Asn Arg Tyr Leu
            900                 905
```